US009260509B2

(12) United States Patent
Mizel et al.

(10) Patent No.: US 9,260,509 B2
(45) Date of Patent: Feb. 16, 2016

(54) **FLAGELLIN FUSION PROTEINS AND USE THEREOF TO INDUCE IMMUNE RESPONSES AGAINST *PSEUDOMONAS AERUGINOSA***

(71) Applicant: Wake Forest University Health Sciences, Winston-Salem, NC (US)

(72) Inventors: Steven B. Mizel, Lewisville, NC (US); Daniel J. Wozniak, Winston-Salem, NC (US); Eric T. Weimer, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 14/750,436

(22) Filed: Jun. 25, 2015

(65) Prior Publication Data

US 2015/0368303 A1 Dec. 24, 2015

Related U.S. Application Data

(62) Division of application No. 13/256,882, filed as application No. PCT/US2010/027460 on Mar. 16, 2010, now Pat. No. 9,096,659.

(60) Provisional application No. 61/210,392, filed on Mar. 18, 2009.

(51) Int. Cl.
*C07H 21/04* (2006.01)
*C07K 16/12* (2006.01)
*A61K 39/104* (2006.01)
*C07K 14/21* (2006.01)
*C12N 15/62* (2006.01)
*C12N 15/63* (2006.01)
*A61K 39/00* (2006.01)

(52) U.S. Cl.
CPC ............ *C07K 16/1214* (2013.01); *A61K 39/104* (2013.01); *C07K 14/21* (2013.01); *C12N 15/62* (2013.01); *C12N 15/63* (2013.01); *A61K 2039/55516* (2013.01); *A61K 2039/6068* (2013.01); *C07K 2317/34* (2013.01); *C07K 2319/00* (2013.01)

(58) Field of Classification Search
None
See application file for complete search history.

(56) References Cited

U.S. PATENT DOCUMENTS

| 6,300,102 | B1 | 10/2001 | Knapp et al. |
| 2003/0232055 | A1 | 12/2003 | Medzhitov |
| 2006/0088555 | A1 | 4/2006 | Sotomayor et al. |
| 2008/0248068 | A1 | 10/2008 | Ljunggren et al. |

FOREIGN PATENT DOCUMENTS

WO WO 2005/077408 A2 8/2005

OTHER PUBLICATIONS

Arnold et al. "Enhanced Immunogenicity in the Murine Airway Mucosa with an Attenuated *Salmonella* Live Vaccine Expressing OprF-Oprl from *Pseudomonas aeruginosa*" *Infection and Immunity* 72(11):6546-6553 (2004).
Bates et al. "Mucosal Adjuvant Activity of Flagellin in Aged Mice" *Mechanisms of Aging and Development* 129(5):271-281 (2008).
Brimer et al. "Cloning and Comparison of *fliC* Genes and Identification of Glycosylation in the Flagellin of *Pseudomonas aeruginosa* a-Type Strains" *Journal of Bacteriology* 180(12):3209-3217 (1998).
Centers for Disease Control and Prevention "Vaccine Safety" www.cdc.gov/vaccinesafety/Concerns/adjuvants.html 2 pages (2010).
Cuadros et al. "Flagellin Fusion Proteins as Adjuvants or Vaccines Induce Specific Immune Responses" *Infection and Immunity* 72(5):2810-2816 (2004).
Döring et al. "A double-blind randomized placebo-controlled phase III study of a *Pseudomonas aeruginosa* flagella vaccine in cystic fibrosis patients" *Proceedings of the National Academy of Sciences* 104(26):11020-11025 (2007).
Duchêne et al. "Sequence and Transcriptional Start Site of the *Pseudomonas aeruginosa* Outer Membrane Porin Protein F Gene" *Journal of Bacteriology* 170(1):155-162 (1988).
Duchêne et al. "*Pseudomonas aeruginosa* Outer Membrane Lipoprotein I Gene: Molecular Cloning, Sequence, and Expression in *Escherichia coli* " *Journal of Bacteriology* 171(8):4130-4137 (1989).
Eaves-Pyles et al. "*Salmonella* Flagellin-Dependent Proinflammatory Responses Are Localized to the Conserved Amino and Carboxyl Regions of the Protein" *The Journal of Immunology* 167:7009-7016 (2001).
Finke et al. "Protection of Immunosuppressed Mice against Infection with *Pseudomonas aeruginosa* by Recombinant *P. aeruginosa* Lipoprotein I and Lipoprotein I-Specific Monoclonal Antibodies" *Infection and Immunity* 59(4):1251-1254 (1991).
Gilleland et al. "Synthetic Peptides Representing Two Protective, Linear B-Cell Epitopes of Outer Membrane Protein F of *Pseudomonas aeruginosa* Elicit Whole-Cell-Reactive Antibodies That Are Functionally Pseudomonad Specific" *Infection and Immunity* 63(6):2347-2351 (1995).
Holder et al. "Experimental Studies of the Pathogenesis of Infections due to *Pseudomonas aeruginosa*: Immunization Using Divalent Flagella Preparations" *The Journal of Trauma* 26(2):118-122 (1986).
Honko et al. "Mucosal Administration of Flagellin Induces Innate Immunity in the Mouse Lung" *Infection and Immunity* 72(11):6676-6679 (2004).
Honko et al. "Effects of Flagellin on Innate and Adaptive Immunity" *Immunologic Research* 33(1):83-101 (2005).

(Continued)

*Primary Examiner* — Patricia A Duffy
(74) *Attorney, Agent, or Firm* — Myers Bigel Sibley & Sajovec, P.A.

(57) ABSTRACT

The invention provides compositions and fusion proteins comprising a flagellin adjuvant and a *Pseudomonas aeruginosa* antigen. The invention further provides pharmaceutical formulations and methods for inducing an immune response against *P. aeruginosa* (e.g., to prevent and/or treat *P. aeruginosa* infection).

18 Claims, 14 Drawing Sheets

(56) References Cited

OTHER PUBLICATIONS

Honko et al. "Flagellin is an Effective Adjuvant for Immunization against Lethal Respiratory Challenge with *Yersinia pestis*" *Infection and Immunity* 74(2):1113-1120 (2006).

Hughes et al. "Synthetic Peptides Representing Epitopes of Outer Membrane Protein F of *Pseudomonas aeruginosa* That Elicit Antibodies Reactive with Whole Cells of Heterologous Immunotype Strains of *P. aeruginosa*" *Infection and Immunity* 60(9):3497-3503 (1992).

Huleatt et al. "Vaccination with recombinant fusion proteins incorporating Toll-like receptor ligands induces rapid cellular and humoral immunity" *Vaccine* 25:763-775 (2007).

Iino, Tetsuo "Genetics of Structure and Function of Bacterial Flagella" *Annual Review of Genetics* 11:161-182 (1977).

International Preliminary Report on Patentability corresponding to International Application No. PCT/US2010/027460:8 pages (mailed Sep. 29, 2011).

International Search Report corresponding to International Application No. PCT/US2010/027460:17 pages (mailed Aug. 5, 2010).

Mansouri et al. "Safety and Immunogenicity of a *Pseudomonas aeruginosa* Hybrid Outer Membrane Protein F-I Vaccine in Human Volunteers" *Infection and Immunity* 67(3):1461-1470 (1999).

Mansouri et al. "Clinical study to assess the immunogenicity and safety of a recombinant *Pseudomonas aeruginosa* OprF-OprI vaccine in burn patients" *FEMS Immunology and Medical Microbiology* 37:161-166 (2003).

McSorley et al. "Bacterial Flagellin Is an Effective Adjuvant for CD4+ T Cells In Vivo" *The Journal of Immunology* 169:3914-3919 (2002).

Mimori-Kiyosue et al. "Locations of terminal segments of flagellin in the filament structure and their roles in polymerization and polymorphism" *Journal of Molecular Biology* 270(2):222-237 (1997) (Abstract Only).

Mizel et al. "Flagellin-F1-V Fusion Protein Is an Effective Plague Vaccine in Mice and Two Species of Nonhuman Primates" *Clinical and Vaccine Immunology* 16(1):21-28 (2009).

Mizel et al. "Flagellin as an Adjuvant: Cellular Mechanisms and Potential" *The Journal of Immunology* 185:5677-5682 (2010).

Neville et al. "Antibodies raised against N'-terminal *Pseudomonas aeruginosa* flagellin prevent mortality in lethal murine models of infection" *International Journal of Molecular Medicine* 16:165-171 (2005).

Saha et al. "Multivalent DNA vaccine protects mice against pulmonary infection caused by *Pseudomonas aeruginosa*" *Vaccine* 24:6240-6249 (2006).

Saha et al. "Blocking of the TLR5 Activation Domain Hampers Protective Potential of Flagellin DNA Vaccine" *The Journal of Immunology* 179:1147-1154 (2007).

Schoenhals et al. "Comparative Analysis of Flagellin Sequences from *Escherichia coli* Strains Possessing Serologically Distinct Flagellar Filaments with a Shared Complex Surface Pattern" *Journal of Bacteriology* 175(17):5395-5402 (1993).

Totten et al. "Characterization of the Type of Flagellin Gene from *Pseudomonas aeruginosa* PAK" *Journal of Bacteriology* 172(12):7188-7199 (1990).

Von Specht et al. "Protection of Immunocompromised Mice against Lethal Infection with *Pseudomonas aeruginosa* by Active or Passive Immunization with Recombinant *P. aeruginosa* Outer Membrane Protein F and Outer Membrane Protein I Fusion Proteins" *Infection and Immunity* 63(5):1855-1862 (1995).

Weimer et al. "A Fusion Protein Vaccine Containing OprF Epitope 8, OprI, and Type A and B Flagellins Promotes Enhanced Clearance of Nonmucoid *Pseudomonas aeruginosa*" *Infection and Immunity* 77(6):2356-2366 (2009).

Weimer et al. "Immunization of young African green monkeys with OprF epitope 8-OprI-type A- and B-flagellin fusion proteins promotes the production of protective antibodies against nonmucoid *Pseudomonas aeruginosa*" *Vaccine* 27:6762-6769 (2009).

Winstanley et al. "Molecular cloning of two *Pseudomonas* flagellin genes and basal body structural genes" *Microbiology* 140:2019-2031 (1994).

Worgall et al. "Protection against *P. aeruginosa* with an adenovirus vector containing an OprF epitope in the capsid" *The Journal of Clinical Investigation* 115(5):1281-1289 (2005).

Worgall et al. "Protective Immunity to *Pseudomonas aeruginosa* Induced with a Capsid-Modified Adenovirus Expressing *P. aeruginosa* OprF" *Journal of Virology* 81(24):13801-13808 (2007).

Zhang et al. "Toll-like Receptor 5-Mediated Corneal Epithelial Inflammatory Responses to *Pseudomonas aeruginosa* Flagellin" *Investigative Ophthalmology & Visual Science* 44(10):4247-4254 (2003).

SEQUENCE LISTING

```
<160> NUMBER OF SEQ ID NOS: 9

<210> SEQ ID NO 1
<211> LENGTH: 14
<212> TYPE: PRT
<213> ORGANISM: Pseudomonas aeruginosa

<400> SEQUENCE: 1

Asn Ala Thr Ala Glu Gly Arg Ala Ile Asn Arg Arg Val Glu
1               5                   10

<210> SEQ ID NO 2
<211> LENGTH: 14
<212> TYPE: PRT
<213> ORGANISM: Pseudomonas aeruginosa

<400> SEQUENCE: 2

Thr Asp Ala Tyr Asn Gln Lys Leu Ser Glu Arg Arg Ala Asn
1               5                   10

<210> SEQ ID NO 3
<211> LENGTH: 31
```

```
<212> TYPE: PRT
<213> ORGANISM: Pseudomonas aeruginosa

<400> SEQUENCE: 3

Glu Gly Gly Arg Val Asn Ala Val Gly Tyr Gly Glu Ser Arg Pro Val
 1               5                  10                  15

Ala Asp Asn Ala Thr Ala Glu Gly Arg Ala Ile Asn Arg Arg Val
            20                  25                  30

<210> SEQ ID NO 4
<211> LENGTH: 12
<212> TYPE: PRT
<213> ORGANISM: Artificial
<220> FEATURE:
<223> OTHER INFORMATION: TLR5-binding immunomodulatory flagellin peptide
      sequence

<400> SEQUENCE: 4

Gly Ala Val Gln Asn Arg Phe Asn Ser Ala Ile Thr
 1               5                  10

<210> SEQ ID NO 5
<211> LENGTH: 1488
<212> TYPE: DNA
<213> ORGANISM: Artificial
<220> FEATURE:
<223> OTHER INFORMATION: OprF-OprI-A-Flagellin coding sequence

<400> SEQUENCE: 5
atggaaggtg gtcgcgtgaa cgctgttggt tacggcgagt cccgcccggt tgccgacaac      60
gccaccgctg aaggccgcgc tatcaaccgt cgcgttggcg gtggcggtgg atccagcagc     120
cactccaaag aaaccgaagc tcgtctgacc gctaccgaag acgcagctgc tcgtgctcag     180
gctcgcgctg acgaagccta tcgcaaggct gacgaagctc tgggcgctgc tcagaaagct     240
cagcagactg ctgacgaggc taacgagcgt gccctgcgca tgctggaaaa agccagccgc     300
aagaagcttg ccttgaccgt caacaccaac atcgcttcgc tgaacactca gcggaacctg     360
aacaactctt ccgcgtcgct gaacacttcg ctgcagcgtc tgtccaccgg ttcgcgcatc     420
aacagcgcca aggacgacgc cgccggcctg cagatcgcca accgtctgac cagccaggtc     480
aacggcctga acgtggctac caagaacgcc aacgacggta tctccctggc gcagaccgct     540
gaaggcgccc tgcagcagtc gaccaacatc ctgcagcgta tgcgtgacct gtccctgcag     600
tcggccaacg gctccaacag cgactccgag cgtaccgctc tgaacggcga agcgaagcaa     660
ctgcagaaag aactggatcg tatcagcaac accaccacct tcggtggccg caagctgctc     720
gacggttcct tcggcgtcgc cagcttccag gtgggttcgg ccgccaacga aatcatcagc     780
gtcggcatcg acgagatgag cgcagagtcg ctgaacggca cctacttcaa ggctgacggc     840
ggcggcgcgg tcactgctgc aaccgcttcg ggcaccgtcg acatcgcgat cggcatcacc     900
ggcggcagcg ccgtgaacgt caaggtcgac atgaagggca cgaaaccgc cgagcaggcg     960 gctgccaaga tcgccgcagc ggtcaacgac gccaacgtcg gcatcggtgc cttcagcgac    1020
ggcgatacca tcagctatgt ttccaaagct ggcaaggatg gctccggtgc gatcactagc    1080
gcggtttccg cgttgtcat cgctgacacc ggcagcaccg cgtaggcac gcggctggc    1140 gtagcccctt ccgctaccgc tttcgccaag accaacgaca ccgtcgccaa gatcgacatc    1200
tccaccgcga aggcgctcag tgccgtgct ggtgatcgca cgacggcgat caagcagatc    1260
gacgccagcg tgccgacctc ggtcgcggtg cagaaccgct tcgacaacac catcaacaac    1320
```

```
ctgaagaaca tcggtgagaa cgtatcggct gctcgcggcc ggatcgaaga caccgacttc    1380
gcagccgaaa ccgccaacct gaccaagaac caagtgctgc aacaagccgg caccgcgatc    1440
ctggcccagg ccaaccagct gccgcagtcg gttctgagcc tgctgcgc                 1488
```

<210> SEQ ID NO 6
<211> LENGTH: 496
<212> TYPE: PRT
<213> ORGANISM: Artificial
<220> FEATURE:
<223> OTHER INFORMATION: OprF-OprI-A-Flagellin aminio acid sequence

<400> SEQUENCE: 6

```
Met Glu Gly Gly Arg Val Asn Ala Val Gly Tyr Gly Glu Ser Arg Pro
1               5                   10                  15

Val Ala Asp Asn Ala Thr Ala Glu Gly Arg Ala Ile Asn Arg Arg Val
            20                  25                  30

Gly Gly Gly Gly Gly Ser Ser Ser His Ser Lys Glu Thr Glu Ala Arg
        35                  40                  45

Leu Thr Ala Thr Glu Asp Ala Ala Arg Ala Gln Ala Arg Ala Asp
    50                  55                  60

Glu Ala Tyr Arg Lys Ala Asp Glu Ala Leu Gly Ala Ala Gln Lys Ala
65                  70                  75                  80

Gln Gln Thr Ala Asp Glu Ala Asn Glu Arg Ala Leu Arg Met Leu Glu
                85                  90                  95

Lys Ala Ser Arg Lys Lys Leu Ala Leu Thr Val Asn Thr Asn Ile Ala
            100                 105                 110

Ser Leu Asn Thr Gln Arg Asn Leu Asn Asn Ser Ser Ala Ser Leu Asn
        115                 120                 125

Thr Ser Leu Gln Arg Leu Ser Thr Gly Ser Arg Ile Asn Ser Ala Lys
    130                 135                 140

Asp Asp Ala Ala Gly Leu Gln Ile Ala Asn Arg Leu Thr Ser Gln Val
145                 150                 155                 160

Asn Gly Leu Asn Val Ala Thr Lys Asn Ala Asn Asp Gly Ile Ser Leu
                165                 170                 175

Ala Gln Thr Ala Glu Gly Ala Leu Gln Gln Ser Thr Asn Ile Leu Gln
            180                 185                 190

Arg Met Arg Asp Leu Ser Leu Gln Ser Ala Asn Gly Ser Asn Ser Asp
        195                 200                 205

Ser Glu Arg Thr Ala Leu Asn Gly Glu Ala Lys Gln Leu Gln Lys Glu
    210                 215                 220

Leu Asp Arg Ile Ser Asn Thr Thr Phe Gly Gly Arg Lys Leu Leu
225                 230                 235                 240

Asp Gly Ser Phe Gly Val Ala Ser Phe Gln Val Gly Ser Ala Ala Asn
                245                 250                 255

Glu Ile Ile Ser Val Gly Ile Asp Glu Met Ser Ala Glu Ser Leu Asn
            260                 265                 270

Gly Thr Tyr Phe Lys Ala Asp Gly Gly Gly Ala Val Thr Ala Ala Thr
        275                 280                 285

Ala Ser Gly Thr Val Asp Ile Ala Ile Gly Ile Thr Gly Gly Ser Ala
    290                 295                 300

Val Asn Val Lys Val Asp Met Lys Gly Asn Glu Thr Ala Glu Gln Ala
305                 310                 315                 320

Ala Ala Lys Ile Ala Ala Ala Val Asn Asp Ala Asn Val Gly Ile Gly
                325                 330                 335
```

```
Ala Phe Ser Asp Gly Asp Thr Ile Ser Tyr Val Ser Lys Ala Gly Lys
            340                 345                 350

Asp Gly Ser Gly Ala Ile Thr Ser Ala Val Ser Gly Val Val Ile Ala
        355                 360                 365

Asp Thr Gly Ser Thr Gly Val Gly Thr Ala Ala Gly Val Ala Pro Ser
    370                 375                 380

Ala Thr Ala Phe Ala Lys Thr Asn Asp Thr Val Ala Lys Ile Asp Ile
385                 390                 395                 400

Ser Thr Ala Lys Ala Leu Ser Arg Arg Ala Gly Asp Arg Thr Thr Ala
                405                 410                 415

Ile Lys Gln Ile Asp Ala Ser Val Pro Thr Ser Val Ala Val Gln Asn
            420                 425                 430

Arg Phe Asp Asn Thr Ile Asn Asn Leu Lys Asn Ile Gly Glu Asn Val
        435                 440                 445

Ser Ala Ala Arg Gly Arg Ile Glu Asp Thr Asp Phe Ala Ala Glu Thr
    450                 455                 460

Ala Asn Leu Thr Lys Asn Gln Val Leu Gln Ala Gly Thr Ala Ile
465                 470                 475                 480

Leu Ala Gln Ala Asn Gln Leu Pro Gln Ser Val Leu Ser Leu Leu Arg
                485                 490                 495

<210> SEQ ID NO 7
<211> LENGTH: 1770
<212> TYPE: DNA
<213> ORGANISM: Artificial
<220> FEATURE:
<223> OTHER INFORMATION: OprF-OprI-B-Flagellin coding sequence

<400> SEQUENCE: 7
atggaaggtg gtcgcgtgaa cgctgttggt tacggcgagt cccgcccggt tgccgacaac      60
gccaccgctg aaggccgcgc tatcaaccgt cgcgttggcg gtggcggtgg atccagcagc     120
cactccaaag aaaccgaagc tcgtctgacc gctaccgaag acgcagctgc tcgtgctcag     180
gctcgcgctg acgaagccta cgcaaggct gacgaagctc tgggcgctgc tcagaaagct     240
cagcagactg ctgacgaggc taacgagcgt gccctgcgca tgctggaaaa agccagccgc     300
aagaagcttg cccttacagt caacacgaac attgcttccc tgaacactca gcgcaacctg     360
aatgcttctt ccaacgacct caacacctcg ttgcagcgtc tgaccaccgg ctaccgcatc     420
aacagtgcca aggacgatgc tgccggcctg cagatctcca accgcctgtc caaccagatc     480
agcggtctga acgttgccac cgcaacgcc aacgacggca tctccctggc cagaccgct      540 gaaggtgccc tgcagcagtc caccaatatc ctgcagcgta tccgcgacct ggccctgcaa     600
tccgccaacg gctccaacag cgacgccgac cgtgccgccc tgcagaaaga gtcgctgcg      660 caacaggccg aactgaccg tatctccgat accaccacct tcggtggccg caagctgctc     720
gacggctcct tcggcaccac cagcttccag gtcggttcca acgcctacga gaccattgac     780
atcagcctgc agaatgcctc tgccagcgcc atcggttctt accaggtcgg cagcaacggc     840
gcgggtaccg tcgccagcgt agcgggcacc gcgaccgctt cgggcatcgc ctcgggcacc     900
gtcaacctgg tcggtggcgg tcaggtgaag aacatcgcca tcgccgccgg cgatagcgcc     960
aaggccatcg ccgagaagat ggacggtgcg atcccgaacc tgtcggctcg tgcccgtacc    1020
gtgttcaccg ctgatgtcag cggcgtgacc ggtggttcgc tgaacttcga cgtaaccgtt    1080
ggcagcaaca ccgtgagcct ggcaggcgtg acctccactc aggatctggc cgaccaactg    1140
aactccaact cgtcgaagct gggcatcact gccagcatca acgacaaggg tgtactgacc    1200
```

```
atcacctccg ctaccggcga gaacgtcaag ttcggtgcgc agaccggtac cgctactgcc   1260
ggtcaggtcg cagtgaaggt ccagggttcc gacggcaagt cgaagcggc cgccaagaac   1320 gtggtagctg ccggtactgc cgctaccacc accatcgtga ccggctacgt gcaactgaac   1380
tcgccgaccg cctactcggt cagcggtacc ggcacccagg cttcgcaggt cttcggcaac   1440
gccagcgccg cgcagaagag cagcgttgcc agcgtcgaca tctccactgc cgacggcgcc   1500
cagaacgcca tcgcggtagt cgataacgcc ctggctgcga tcgacgccca gcgtgctgac   1560
ctcggtgctg ttcagaaccg cttcaagaac actatcgaca acctgaccaa catctcggaa   1620
aacgctacca acgctcgtag ccgcatcaag gacaccgact cgctgccga aaccgcggcg   1680 ctgtcgaaga accaggtgct gcaacaggcc ggtaccgcga tcctggccca ggccaaccag   1740
ctgccgcagg cggtcctgag cctgctgcgc                                    1770
```

<210> SEQ ID NO 8
<211> LENGTH: 590
<212> TYPE: PRT
<213> ORGANISM: Artificial
<220> FEATURE:
<223> OTHER INFORMATION: OprF-OprI-B-Flagellin amino acid sequence

<400> SEQUENCE: 8

```
Met Glu Gly Gly Arg Val Asn Ala Val Gly Tyr Gly Glu Ser Arg Pro
1               5                   10                  15

Val Ala Asp Asn Ala Thr Ala Glu Gly Arg Ala Ile Asn Arg Arg Val
            20                  25                  30

Gly Gly Gly Gly Ser Ser His Ser Lys Glu Thr Glu Ala Arg
        35                  40                  45

Leu Thr Ala Thr Glu Asp Ala Ala Ala Arg Ala Gln Ala Arg Ala Asp
    50                  55                  60

Glu Ala Tyr Arg Lys Ala Asp Glu Ala Leu Gly Ala Ala Gln Lys Ala
65                  70                  75                  80

Gln Gln Thr Ala Asp Glu Ala Asn Glu Arg Ala Leu Arg Met Leu Glu
                85                  90                  95

Lys Ala Ser Arg Lys Lys Leu Ala Leu Thr Val Asn Thr Asn Ile Ala
            100                 105                 110

Ser Leu Asn Thr Gln Arg Asn Leu Asn Ala Ser Ser Asn Asp Leu Asn
        115                 120                 125

Thr Ser Leu Gln Arg Leu Thr Thr Gly Tyr Arg Ile Asn Ser Ala Lys
    130                 135                 140

Asp Asp Ala Ala Gly Leu Gln Ile Ser Asn Arg Leu Ser Asn Gln Ile
145                 150                 155                 160

Ser Gly Leu Asn Val Ala Thr Arg Asn Ala Asn Asp Gly Ile Ser Leu
                165                 170                 175

Ala Gln Thr Ala Glu Gly Ala Leu Gln Gln Ser Thr Asn Ile Leu Gln
            180                 185                 190

Arg Ile Arg Asp Leu Ala Leu Gln Ser Ala Asn Gly Ser Asn Ser Asp
        195                 200                 205

Ala Asp Arg Ala Ala Leu Gln Lys Glu Val Ala Ala Gln Gln Ala Glu
    210                 215                 220

Leu Thr Arg Ile Ser Asp Thr Thr Phe Gly Gly Arg Lys Leu Leu
225                 230                 235                 240

Asp Gly Ser Phe Gly Thr Thr Ser Phe Gln Val Gly Ser Asn Ala Tyr
                245                 250                 255
```

```
Glu Thr Ile Asp Ile Ser Leu Gln Asn Ala Ser Ala Ser Ala Ile Gly
            260                 265                 270

Ser Tyr Gln Val Gly Ser Asn Gly Ala Gly Thr Val Ala Ser Val Ala
        275                 280                 285

Gly Thr Ala Thr Ala Ser Gly Ile Ala Ser Gly Thr Val Asn Leu Val
    290                 295                 300

Gly Gly Gly Gln Val Lys Asn Ile Ala Ile Ala Ala Gly Asp Ser Ala
305                 310                 315                 320

Lys Ala Ile Ala Glu Lys Met Asp Gly Ala Ile Pro Asn Leu Ser Ala
                325                 330                 335

Arg Ala Arg Thr Val Phe Thr Ala Asp Val Ser Gly Val Thr Gly Gly
            340                 345                 350

Ser Leu Asn Phe Asp Val Thr Val Gly Ser Asn Thr Val Ser Leu Ala
        355                 360                 365

Gly Val Thr Ser Thr Gln Asp Leu Ala Asp Gln Leu Asn Ser Asn Ser
    370                 375                 380

Ser Lys Leu Gly Ile Thr Ala Ser Ile Asn Asp Lys Gly Val Leu Thr
385                 390                 395                 400

Ile Thr Ser Ala Thr Gly Glu Asn Val Lys Phe Gly Ala Gln Thr Gly
                405                 410                 415

Thr Ala Thr Ala Gly Gln Val Ala Val Lys Val Gln Gly Ser Asp Gly
            420                 425                 430

Lys Phe Glu Ala Ala Ala Lys Asn Val Val Ala Ala Gly Thr Ala Ala
        435                 440                 445

Thr Thr Thr Ile Val Thr Gly Tyr Val Gln Leu Asn Ser Pro Thr Ala
    450                 455                 460

Tyr Ser Val Ser Gly Thr Gly Thr Gln Ala Ser Gln Val Phe Gly Asn
465                 470                 475                 480

Ala Ser Ala Ala Gln Lys Ser Ser Val Ala Ser Val Asp Ile Ser Thr
                485                 490                 495

Ala Asp Gly Ala Gln Asn Ala Ile Ala Val Val Asp Asn Ala Leu Ala
            500                 505                 510

Ala Ile Asp Ala Gln Arg Ala Asp Leu Gly Ala Val Gln Asn Arg Phe
        515                 520                 525

Lys Asn Thr Ile Asp Asn Leu Thr Asn Ile Ser Glu Asn Ala Thr Asn
    530                 535                 540

Ala Arg Ser Arg Ile Lys Asp Thr Asp Phe Ala Ala Glu Thr Ala Ala
545                 550                 555                 560

Leu Ser Lys Asn Gln Val Leu Gln Gln Ala Gly Thr Ala Ile Leu Ala
                565                 570                 575

Gln Ala Asn Gln Leu Pro Gln Ala Val Leu Ser Leu Leu Arg
            580                 585                 590
```

<210> SEQ ID NO 9
<211> LENGTH: 63
<212> TYPE: PRT
<213> ORGANISM: Pseudomonas aeruginosa

<400> SEQUENCE: 9

```
Ser Ser His Ser Lys Glu Thr Glu Ala Arg Leu Thr Ala Thr Glu Asp
1               5                   10                  15

Ala Ala Ala Arg Ala Gln Ala Arg Ala Asp Glu Ala Tyr Arg Lys Ala
                20                  25                  30

Asp Glu Ala Leu Gly Ala Ala Gln Lys Ala Gln Gln Thr Ala Asp Glu
            35                  40                  45
```

```
Ala Asn Glu Arg Ala Leu Arg Met Leu Glu Lys Ala Ser Arg Lys
 50                  55                  60
```

FLAGELLIN FUSION PROTEINS AND USE THEREOF TO INDUCE IMMUNE RESPONSES AGAINST *PSEUDOMONAS AERUGINOSA*

RELATED APPLICATION INFORMATION

This application is a divisional of U.S. patent application Ser. No. 13/256,882, filed Nov. 30, 2011 which claims priority under 35 U.S.C. 371 from PCT Application No. PCT/US2010/027460, filed Mar. 16, 2010, which claims the benefit of U.S. Provisional Application No. 61/210,392, filed Mar. 18, 2009, the disclosures of which are incorporated by reference herein in their entireties.

STATEMENT OF GOVERNMENT SUPPORT

This invention was supported in part by funding provided under Grant No. AI061396 from the National Institutes of Health. The United States government has certain rights in this invention.

FIELD OF THE INVENTION

The present invention concerns the use of a flagellin adjuvant, antigens from *Pseudomonas aeruginosa* and fusion proteins and compositions comprising the same to produce an immune response against *P. aeruginosa* (e.g., in the prevention and/or treatment of *P. aeruginosa* infection).

STATEMENT REGARDING ELECTRONIC FILING OF A SEQUENCE LISTING

A Sequence Listing in ASCII text format, submitted under 37 C.F.R. §1.821, entitled 9151-121_ST25.txt, 16,060 bytes in size, generated on Aug. 1, 2013 and filed via EFS-Web, is provided in lieu of a paper copy. This Sequence Listing is hereby incorporated by reference into the specification for its disclosures.

BACKGROUND OF THE INVENTION

Cystic fibrosis (CF) is a hereditary disease that is linked to a defective cystic fibrosis transmembrane receptor (CFTR) (Raman et al., (2002) Pediatrics 109: e19. In CF patients, the presence of a defective CFTR protein leads to dehydrated mucosal surfaces and disruption of ion transport. In the initial stages of disease, CF patients are infected with *Staphylococcus aureus* and *Hemophilus influenzae*, but eventually become infected with nonmucoid *Pseudomonas aeruginosa*, a gram-negative opportunistic pathogen that is the major cause of morbidity and mortality in these patients (Burns et al., (2001) *J. Infectious Diseases* 183:444-452; Koch, (2002) *Pediatr. Pulmonol.* 34:232-236; Li et al., (2005) *JAMA* 293: 581-588; Tosi et al., (1995) *J. Infectious Diseases* 172:453-461). Following colonization, *P. aeruginosa* undergoes a mucoid conversion to an alginate-overexpressing phenotype that is associated with biofilm development and enhanced resistance to antibiotic therapy (Li et al., (2005) *JAMA* 293: 581-588). CF is characterized by lung inflammation mediated, in part, by chronic *P. aeruginosa* infection. *P. aeruginosa* possess numerous virulence factors that facilitate evasion of the immune system (Frank et al., (2002). *J. Infectious Diseases* 186: 64-73; Morici et al., (2007) *J. Bacteriology* 189:7752-7764; Nicas & Iglewski, (1985) *Can. J. Microbiol.* 31:387-392; Sadikot et al., (2005) *Am. J. Respiratory and Critical Care Medicine* 171:1209-12223). For example, *P. aeruginosa* secrete enzymes such as alkaline protease and elastase, which degrade complement components and thus limit the role of complement in the clearance of early pulmonary *P. aeruginosa* infections (Gross et al., (1978) *J. Clin. Invest.* 62:373-378). The critical role of complement in the clearance of *P. aeruginosa* is evidenced by the observation that C3 and C5 knock-out (KO) mice were unable to clear *P. aeruginosa* after challenge (Mueller-Prtiz et al., (2004) *Infect. Immun.* 72:2899-2906; Younger et al., (2003) *Am. J. Resp. Cell Molecular Biology* 29:432-438). In addition, *P. aeruginosa* express LPS variants that interfere with C3b deposition (Schiller, (1988) *Infect. Immun.* 56:632-639).

Initial efforts to develop a *P. aeruginosa* vaccine focused primarily on LPS. Although vaccination with *P. aeruginosa* lipopolysaccharide (LPS) was effective in several animal models and led to the production of highly opsonic antibodies, the efficacy in human trials was limited by antigenic diversity of O-antigens among *P. aeruginosa* (DiQiandomenico et al., (2007) *Proc. Nat. Acad. Sci. USA* 104:4624-4629).

*P. aeruginosa* possesses two types of flagellins, type-A and type-B that differ in amino acid composition and length of the hypervariable region. A phase III clinical trial of *P. aeruginosa* flagella in CF patients demonstrated that the vaccine was well tolerated, but only resulted in a 30% reduction in the incidence of infection (airing et al., (2007) *Proc. Nat. Acad. Sci.* 104:11020-11025). In related studies, immunization with the OprI antigen of *P. aeruginosa* and an alum adjuvant elicited a protective response in mice that correlates with the titer of OprI-specific IgG (Finke et al., (1990) Infect. Immun. 58:2241-2244). In addition, an adenovirus expressing epitope 8 (amino acids 310-340) (Epi8) of OprF provided protection against acute *P. aeruginosa* infection (Worgall et al., (2007) *J. Virol.* 81:13801-13808; Worgall et al., (2005) *J. Clin. Invest.* 115:1281-1289). Several investigators have focused on a fusion peptide containing OprF and OprI as a potential vaccine candidate. A study in burn patients revealed that a OprF-OprI fusion peptide was immunogenic and well tolerated (Knapp et al., (1999) *Vaccine* 17:1663-1666; Mansouri et al, (2003) *FEMS Immunology and Medical Microbiology* 37:161-166).

Although these experimental *P. aeruginosa* vaccines have shown some promise in initial clinical trials, none have achieved the level of response required for protection against *P. aeruginosa* in CF patients.

It would be desirable to provide improved reagents, pharmaceutical formulations and methods for producing an immune response against *P. aeruginosa*, for example, to prevent and/or treat infection (e.g., in CF patients, burn patients or ventilated patients).

SUMMARY OF THE INVENTION

The inventors have identified several characteristics for optimization of an effective *Pseudomonas aeruginosa* vaccine: the presence of a potent adjuvant, the ability to induce high titer antigen-specific IgG that exhibits a high degree of functional activity (e.g., complement activation), multivalency, and the ability to induce a robust memory response. Disclosed herein are multivalent vaccines that satisfy one or more of these criteria. The present invention is based, in part, on the discovery that flagellins can function as potent adjuvants (e.g., fusion proteins between a *P. aeruginosa* antigen(s) and a flagellin adjuvant) to enhance the immune response mounted in a subject against *P. aeruginosa* (e.g., to prevent and/or treat *P. aeruginosa* infection). In embodiments of the invention, the inventive flagellin fusion proteins are highly potent, requiring lower protein dosages and eliciting higher titers of protective antibodies (e.g., IgG) as compared with prior vaccines. Further, the flagellin fusion proteins of the invention may have the ability to produce higher quality antibodies (e.g., higher affinity) than prior vaccines.

Accordingly, in particular embodiments, the invention provides a fusion protein comprising:

(a) a *Pseudomonas aeruginosa* type A flagellin adjuvant and/or a *Pseudomonas aeruginosa* type B flagellin adjuvant; and (b) a *Pseudomonas aeruginosa* antigen.

In particular embodiments, the fusion protein comprises a *Pseudomonas aeruginosa* type A flagellin adjuvant and/or a *Pseudomonas aeruginosa* type B flagellin adjuvant; and (b) a *Pseudomonas aeruginosa* OprF antigen and/or a *Pseudomonas aeruginosa* OprI antigen.

In embodiments of the invention, the fusion protein further comprises the *P. aeruginosa* 5-hexose Psi polysaccharide. For example, monomers and/or dimers of the *P. aeruginosa* polysaccharide can be conjugated to one or more of the fusion proteins.

Accordingly, the invention also provides a *P. aeruginosa* type A or type B flagellin adjuvant or fusion protein of the invention conjugated to *P. aeruginosa* Psi polysaccharide.

As a further aspect the invention provides a composition comprising:

(a) a fusion protein comprising (i) a *Pseudomonas aeruginosa* type A flagellin adjuvant; and (ii) a *Pseudomonas aeruginosa* antigen; and (b) a fusion protein comprising (i) a *Pseudomonas aeruginosa* type B flagellin adjuvant; and (ii) a *Pseudomonas aeruginosa* antigen.

In particular embodiments, the composition comprises: (a) a fusion protein comprising (1) a *Pseudomonas aeruginosa* type A flagellin adjuvant; and (ii) a *Pseudomonas aeruginosa* OprF antigen and/or a *Pseudomonas aeruginosa* OprI antigen; and (b) a fusion protein comprising (i) a *Pseudomonas aeruginosa* type B flagellin adjuvant; and (ii) a *Pseudomonas aeruginosa* OprF antigen and/or a *Pseudomonas aeruginosa* OprI antigen.

In embodiments of the invention, the composition further comprises the *P. aeruginosa* 5-hexose Psl polysaccharide, which can be present as free polysaccharide and/or conjugated to a carrier protein. Optionally, one or more flagellin adjuvants and/or fusion proteins of the invention act as the carrier protein and have Psl polysaccharide conjugated thereto. For example, monomers and/or dimers of the *P. aeruginosa* polysaccharide can be conjugated to one or more of the flagellin adjuvants and/or fusion proteins.

As a further aspect, the invention provides a nucleic acid encoding a fusion protein of the invention.

As yet another aspect, the invention provides a vector comprising a nucleic acid of the invention.

The invention also provides host cells comprising the nucleic acids or vectors of the invention.

Still further, the invention provides a method of making a fusion protein of the invention, the method comprising culturing a host cell of the invention in a culture medium under conditions sufficient for the fusion protein to be produced.

As another aspect, the invention provides an immunogenic formulation comprising the fusion protein or composition of the invention in a pharmaceutically acceptable carrier.

As another aspect, the invention provides a method of producing an immune response against *Pseudomonas aeruginosa* in a mammalian subject, the method comprising administering a fusion protein, composition or immunogenic formulation of the invention to the mammalian subject in an amount effective to produce an immune response in the mammalian subject against *Pseudomonas aeruginosa*.

Also provided is a method of protecting a mammalian subject from infection with *Pseudomonas aeruginosa*, the method comprising administering a fusion protein, composition, or immunogenic formulation of the invention to the mammalian subject in an amount effective to protect the mammalian subject from infection with *Pseudomonas aeruginosa*.

As still another aspect, the invention provides a method of enhancing a protective immune response to *Pseudomonas aeruginosa* in a mammalian subject, the method comprising administering a fusion protein, composition, or immunogenic formulation of the invention to the mammalian subject in an amount effective to enhance the protective immune response to *Pseudomonas aeruginosa* in the mammalian subject As yet a further aspect, the invention provides a method of treating a mammalian subject infected with motile, nonmucoid *Pseudomonas aeruginosa*, the method comprising administering a fusion protein, composition, or immunogenic formulation of the invention to the mammalian subject in an amount effective to treat the mammalian subject infected with motile, nonmucoid *Pseudomonas aeruginosa*.

In representative embodiments, the subject is a human subject, optionally a human subject afflicted with cystic fibrosis, afflicted with a burn injury, in an immunocompromised state (e.g., an AIDS patient or cancer patient) and/on a ventilator.

These and other aspects of the invention are set forth in the description of the invention that follows.

BRIEF DESCRIPTION OF THE DRAWINGS

FIG. 2A is a graph on TNF-α production for *P. aeruginosa* A-flagellin and B-flagellin. FIG. 2B is a graph on TNF-α production for OprI-type A and B-flagellin fusions. FIG. 2C is a graph on TNF-α production for $OprF_{311-341}$-OprI-type A and B-flagellin fusions. Data represent the results of three independent experiments done in triplicate.

FIG. 4A shows a graph on the generation of antigen-specific plasma cells and a graph on the generation of antigen-specific memory B cells. FIG. 4B shows a graph on the total number of antigen-specific plasma cells generated and a graph on the total number of antigen-specific memory B cells generated.

FIG. 6A shows graphs on antigen-specific IgG binding to *P. aeruginosa*. Left column—Plasma samples from OprI-Flagellins immunized mice. Filled regions refer to control strain WFPA860 (ΔfliC-ΔoprI) which lacks flagellin and OprI. Right column—Plasma samples from OprF-OprI-Flagellins immunized mice. WT, wild-type; B-Flagellin+, fliC$^+$ΔoprIΔoprF; OprI+, oprI$^+$ΔfliCΔoprF; OprF+, oprF$^+$ΔfliCΔoprI. Filled regions refer to control WFPA864 (ΔfliCΔoprIΔoprF) strain lacking all three antigens. FIG. 6B shows graphs on C3 deposition on *P. aeruginosa* strains. FIG. 6C shows graphs on percent C3 positive of the data shown in FIG. 6B. *=p<0.05, **=p<0.001, compared to WFPA860 (ΔfliCΔoprI) (top) or WFPA864 (ΔfliCΔoprIΔoprF) (bottom). Statistics were performed using Student's t-test. Data are from 2 independent experiments performed in triplicate.

FIG. 9A shows images of the lung sections for OprF-OprI immunized mice. A1-3 magnified 4×. A4 magnified 40× to show bacteria. A5-6 magnified 20×. FIG. 9B shows images of the lung sections for OprF$_{311-341}$-OprI-Flagellins immunized mice. B1-3 magnified 4×. B4-6 magnified 20×. FIG. 9C shows a graph on the score for inflammation from the slides. Slides were blindly scored for consolidation, bronchiolar and vascular degenerative changes, alveolar wall thickness, and edema. The score for inflammation was determined by the sum for each category. Dotted line indicates lowest score possible. *p<0.05, using Student's t-test.

DETAILED DESCRIPTION OF THE INVENTION

Figure 1:
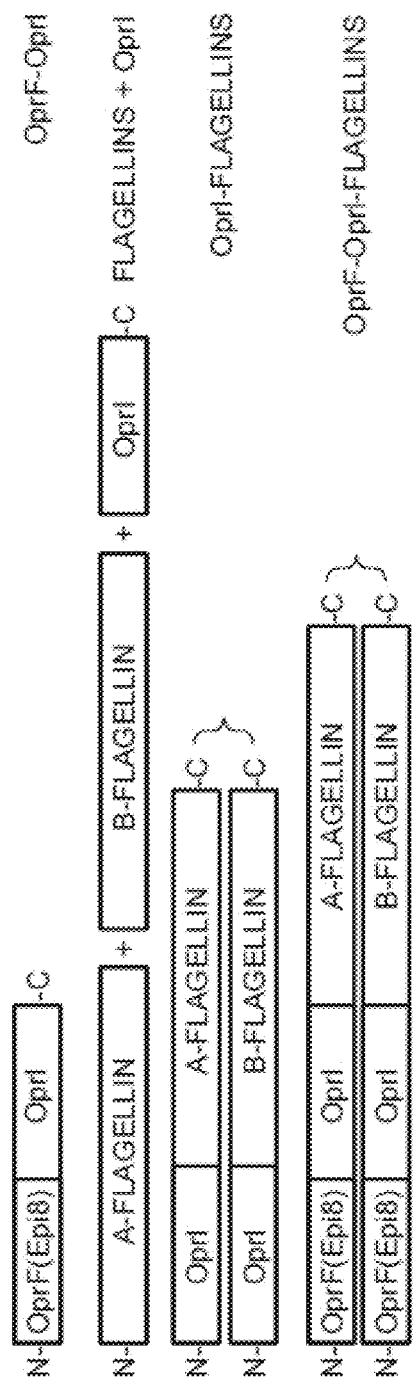
FIG. 1. Illustration of the constructs used in the Examples.

The present invention will now be described with reference to the accompanying drawings, in which representative embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in
the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

As used in the description of the invention and the appended claims, the singular forms "a," "an" and "the" are intended to include the plural forms as well, unless the context clearly indicates otherwise.

The term "about," as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Numerical ranges as described herein are intended to be inclusive unless the context indicates otherwise. For example, the numerical range of "1 to 10" or "1-10" is intended to be inclusive of the values 1 and 10.

Also as used herein, "and/or" refers to and encompasses any and all possible combinations of one or more of the associated listed items, as well as the lack of combinations when interpreted in the alternative ("or").

It is specifically intended that the various aspects of the invention described herein can be used in any combination.

Moreover, the present invention also contemplates that in some embodiments of the invention, any feature or combination of features set forth herein can be excluded or omitted.

By "consisting essentially of" as used herein, it is meant that the indicated peptide, protein, fusion protein, nucleic acid, compound, composition, formulation and the like does not include any other material elements (i.e., elements that materially impact the structure and/or function of the peptide, protein, fusion protein, nucleic acid, compound, composition or formulation).

As used herein, the term "polypeptide" encompasses both peptides and proteins (including fusion proteins), unless indicated otherwise.

As used herein, the terms "enhance," "enhances," and "enhancing" an immune response (and similar terms), optionally a protective immune response, indicate that the immune response (e.g., antigen-specific IgG production), optionally a protective immune response, is increased by at least about 25%, 50%, 2-fold, 3-fold, 4-fold, 5-fold, 10-fold, 15-fold, 20-fold, 30-fold, 40-fold, 50-fold, 60-fold, 75-fold, 100-fold, 150-fold, 500-fold, 1000-fold or more.

As used herein, an amino acid sequence that is "substantially identical" or "substantially similar" to a reference amino acid sequence is at least about 70%, 75%, 80%, 85%, 90%, 95%, 97%, 98% or 99% identical or similar, respectively, to the reference amino acid sequence.

Methods of determining sequence similarity or identity between two or more amino acid sequences are known in the art. Sequence similarity or identity may be determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch, *J. Mol. Biol.* 48, 443 (1970), by the search for similarity method of Pearson & Lipman, *Proc. Natl. Acad. Sci. USA* 85, 2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12, 387-395 (1984), or by inspection.

Another suitable algorithm is the BLAST algorithm, described in Altschul et al., *J. Mol. Biol.* 215, 403-410, (1990) and Karlin et al., *Proc. Natl. Acad. Sci. USA* 90, 5873-5787 (1993). A particularly useful BLAST program is the WU-BLAST-2 program which was obtained from Altschul et al., *Methods in Enzymology*, 266, 460-480 (1996); http://blast.wustl/edu/blast/README.html. WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity.

Further, an additional useful algorithm is gapped BLAST as reported by Altschul et al., (1997) *Nucleic Acids Res.* 25, 3389-3402.

In representative embodiments of the invention, the peptides, proteins, fusion proteins, nucleic acids and/or cells of the invention are "isolated." By "isolated" it is meant that the peptide, protein, fusion protein, nucleic acid and/or cell is at least partially purified away from some of the other components of the naturally occurring organism or virus with which it is naturally associated. To illustrate, unless the context indicates otherwise, the isolated fusion proteins of the invention are generally not incorporated into flagella, either as part of an organism or as isolated flagella. In representative embodiments of the invention and "isolated" peptide, protein or fusion protein is at least about 5%, 10%, 15%, 20%, 25%, 30%, 40%, 50%, 60%, 70%, 75%, 80%, 85%, 90%, 95%, 97%, 98%, 99% pure (w/w) or more.

I. *Pseudomonas aeruginosa* Antigens.

The terms "immunogen" and "antigen" are used interchangeably herein and mean any compound (including polypeptides) to which a cellular and/or humoral immune response can be directed.

Unless indicated otherwise by the context, as used herein the term "*P. aeruginosa* antigen" (and equivalent terms) is not intended to refer to a *P. aeruginosa* flagellin antigen (if present). Although flagellins are very powerful antigens, according to the present invention the flagellin may or may not be from *P. aeruginosa*, and the term "*P. aeruginosa* antigen" (and equivalent terms) is intended to refer to antigens from *P. aeruginosa* that are distinct from any *P. aeruginosa* flagellin antigen that may also be present.

Antigens from *P. aeruginosa* for use in vaccines are well-known in the art. The present invention can be practiced with any suitable *P. aeruginosa* antigen including, without limitation, one or more *P. aeruginosa* *P. aeruginosa* outer membrane protein antigens, PilA antigens and/or PcrV antigens (these terms including the entire polypeptide and active fragments thereof). In particular embodiments, the outer membrane protein antigen is a *P. aeruginosa* porin protein F (OprF) antigen, a *P. aeruginosa* lipoprotein I (OprI) antigen and/or a *P. aeruginosa* protein H2 (OprH2) antigen (these terms including the entire polypeptide and active fragments thereof); or fusions of two or more *P. aeruginosa* antigens (these terms including the entire polypeptide and active fragments thereof). Suitable active fragments generally comprise one or more epitopes that induce an immune response (cellular and/or humoral) and, optionally, confer protection to a subject against *P. aeruginosa*. In representative embodiments, the active fragment comprises all or part of an extracellular portion of the polypeptide.

In embodiments of the invention, an "active fragment" of a *P. aeruginosa* antigen or epitope is at least about 6, 8, 10, 15, 20, 30, 50, 75, 100, 150, 200, 250 or 300 or more contiguous amino acids and/or less than about 300, 250, 200, 150, 100, 75, 50, 30, 20 or 15 contiguous amino acids, including any combination of the foregoing as long as the lower limit is less than the upper limit and induces an immune response (e.g., IgG that react with the native antigen), optionally a protective immune response, against *P. aeruginosa* in a host. In particular embodiments, the active fragment induces an immune response in a host, optionally a protective immune response, that is at least about 50%, 75%, 80%, 85%, 90%, or 95% or more of the immune response induced by the full-length antigen or epitope, or induces an immune response that is the same as or essentially the same as the full-length antigen or epitope, or induces an immune response that is even greater than the immune response induced by the full-length antigen or epitope.

Further, as used herein, a "*P. aeruginosa* antigen" or "antigen from *P. aeruginosa*" or like terms include, without limitation, naturally occurring *P. aeruginosa* antigens and modified forms thereof that induce an immune response in a subject, optionally a protective immune response, against *P. aeruginosa*. For example, a native antigen can be modified to increase safety and/or immunogenicity and/or as a result of cloning procedures or other laboratory manipulations. Further, in embodiments of the invention, the amino acid sequence of the modified form of the *P. aeruginosa* antigen can comprise one, two, three or fewer, four or fewer, five or fewer, six or fewer, seven or fewer, eight or fewer, nine or fewer, ten or fewer modifications, twenty or fewer, or fifty or fewer as compared with the amino acid sequence of the naturally occurring antigen and induce an immune response (optionally a protective immune response) against *P. aeruginosa* in the host. Suitable modifications encompass deletions (including truncations), insertions (including N- and/or C-terminal extensions) and amino acid substitutions, and any combination thereof. In representative embodiments, the *P. aeruginosa* antigen is an antigen that is substantially similar at the amino acid level to the amino acid sequence of a naturally occurring *P. aeruginosa* antigen and induces an immune response (optionally a protective immune response) against *P. aeruginosa* in a host.

In embodiments of the invention, a "modified" *P. aeruginosa* antigen or epitope induces an immune response in a host (e.g., IgG that react with the native antigen), optionally a protective immune response, that is at least about 50%, 75%, 80%, 85%, 90%, or 95% or more of the immune response induced by the native antigen or epitope, or induces an immune response that is the same as or essentially the same as the native antigen or epitope, or induces an immune response that is even greater than the immune response induced by the native antigen or epitope.

In embodiments of the invention, two or more *P. aeruginosa* antigens are provided in the fusion protein and/or immunogenic composition (e.g., 2, 3, 4, 5, 6 or more *P. aeruginosa* antigens), for example, two or more *P. aeruginosa* outer membrane protein antigens such as an OprI antigen and an OprF antigen.

Further, in embodiments of the invention, one or more *P. aeruginosa* antigens can be present in multiple copies (e.g., 2, 3, 4, 5, 6 or more) in the fusion protein and/or immunogenic formulation. For example, a single flagellin fusion protein can comprise two or more copies of a *P. aeruginosa* antigen and/or in a composition comprising multiple flagellin fusion proteins of the invention, a *P. aeruginosa* antigen can be present in two or more of the fusion proteins in the composition.

Those skilled in the art will appreciate that it may be advantageous for the antigen to include one or more B cell epitopes and/or one or more T cell epitopes (e.g., 2, 3, 4, 5, 6, 7, 8, 9, 10 or more B cell epitopes and/or T cell epitopes). Optionally, the *P. aeruginosa* antigen comprises one or more epitopes exposed on the surface of the naturally occurring *P. aeruginosa* protein. In the case of *P. aeruginosa* OprI and/or OprF antigens, these proteins have been well-characterized, including epitope mapping studies (see, e.g., von Specht et al., (1995) *Infection and Immunity* 63:1855-1862; and U.S. Pat. No. 6,300,102; Mansouri et al., (2003) *FEMS Immunology and Medical Microbiology* 37:161-166; and Worgall et al., (2005) *J. Clin. Invest.* 115:1281-1289).

The *P. aeruginosa* OprF protein has been cloned and sequenced (Duchene et al., (1988) *J. Bacteriology* 170:155-162; GenBank Accession No. AAA25973 and Swiss-Prot Accession No. P13794, all of which relate to the amino acid and nucleic acid sequences of the OprF protein of *P. aeruginosa* PAO1). The precursor OprF protein of *P. aeruginosa* is 350 amino acids long; amino acids 1 to 24 are the signal peptide and the mature protein is 326 amino acids long and found at amino acid positions 25 to 350 of the precursor molecule (precursor amino acid sequence at GenBank Accession No. AAA25973 and Swiss-Prot Accession No. P13794; mature amino acid sequence at FIG. 2 of Hughes et al., (1992) *Infect. Immun.* 60: 3497-3503). The carboxy-terminal portion of the *P. aeruginosa* OprF has been reported to contain protective epitopes (e.g., amino acids 190 to 342; Mansouri et al., (2003) *FEMS Immunology and Medical Microbiology* 37:161-166). Further, the *P. aeruginosa* OprF protein contains a number of extracellular loops that contain promising B cell epitopes (Worgall et al., (2005) *J. Clin. Invest.* 115:1281-1289). Nonlimiting examples of B cell epitopes located in *P. aeruginosa* OprF include the B cell epitopes at amino acids 190 to 213; amino acids 212 to 240; amino acids 239 to 250; amino acids 243 to 256; amino acids 284 to 316; amino acids 285 to 298; amino acids 329 to 341, amino acids 329 to 342; amino acids 332-350; amino acids 240-316; and amino acids 190-250 (amino acid numbering with respect to *P. aeruginosa* strain PAO1; see, e.g., von Specht et al., (1995) *Infection and Immunity* 63:1855-1862; U.S. Pat. No. 6,300,102; Worgall et al., (2005) *J. Clin. Invest.* 115:1281-1289; and Worgall et al., (2007) *J. Virol.* 81:13801-13808). Particular epitopes include NATAEGRAINRRVE (SEQ ID NO:1; amino acids 329 to 342 of the OprF precursor protein) and TDAYNQKLSERRAN (SEQ ID NO:2; amino acids 285 to 298 of the OprF precursor protein).

In particular embodiments, the *P. aeruginosa* OprF antigen comprises, consists essentially of or consists of one or more, two or more, three or more, or four or more epitopes (e.g., B cell epitopes and/or T cell epitopes), which may include one or more of the epitopes specifically described herein or orthologs or active fragments thereof. In embodiments of the invention, the *P. aeruginosa* OprF antigen comprises, consists essentially of, or consists of the full-length precursor or mature *P. aeruginosa* OprF protein or, alternatively, an active fragment of either of the foregoing (e.g., at least about 6, 8, 10, 15, 20, 30, 50, 75, 100, 150, 200, 250, 300 or more contiguous amino acids and/or less than about 300, 250, 200, 150, 100, 75, 50, 30, 20, or 15 contiguous amino acids, including any combination of the foregoing as long as the lower limit is less than the upper limit). In embodiments, the *P. aeruginosa* OprF antigen comprises, consists essentially, or consists of a carboxy terminal fragment of the *P. aeruginosa* OprF protein, for example, amino acids 58 to 350; amino acids 179 to 342, amino acids 190 to 342, amino acids 190 to 350 or amino acids 332 to 350 of the OprF precursor (GenBank Accession No. AAA25973 and Swiss-Prot Accession No. P13794; see Mansouri et al., (2003) *FEMS Immunology and Medical Microbiology* 37:161-166; von Specht et al., (1995) *Infection and Immunity* 63:1855-1862; Saha et al. (2006) *Vaccine* 24:6240-6249; and Mansouri et al., (1999) *Infect. Immun.* 67:1461-1470) or orthologs or active fragments thereof. Further, in embodiments of the invention, the *P. aeruginosa* OprF antigen comprises, consists essentially of, or consists of the *P. aeruginosa* OprF antigen described as SEQ ID NO:11 in U.S. Pat. No. 6,300,102 or fragments thereof, e.g., amino acids 1 to 153, amino acids 23 to 51, amino acids 54 to 67, amino acids 96 to 109 and/or amino acids 143 to 161 of SEQ ID NO:11 disclosed in U.S. Pat. No. 6,300,102 or orthologs or active fragments thereof. In other embodiments, the *P. aeruginosa* antigen comprises, consists essentially of, or consists of amino acids 311-341 of the *P. aeruginosa* OprF protein (EGGRVNAVGYGESRPVADNATAEGRAINRRV; SEQ ID NO:3) or orthologs or active fragments thereof.

The *P. aeruginosa* OprI protein has also been cloned and sequenced (Duchene et al., (1989) *J. Bacteriology* 171:4130-4137; von Specht et al., (1995) *Infection and Immunity* 63:1855-1862; U.S. Pat. No. 6,300,102; NCBI Accession No. NP 251543; GenBank Accession No. AAG06241; and Swiss Protein Accession No. P11221, all of which relate to the amino acid and nucleic acid sequences of the OprI precursor protein of *P. aeruginosa* PAO1). The full-length precursor *P. aeruginosa* OprI protein is 83 amino acids long, with a 20 amino acid signal sequence and 63 amino acid mature protein at positions 21-83 (SSHSKETEAR LTATEDAAAR AQARADEAYR KADEALGAAQ KAQQTADEAN ERALRMLEKA SRK, SEQ ID NO:9) of the precursor (Duchene et al., (1989) *J. Bacteriology* 171:4130-4137). Nonlimiting examples of B cell epitopes located in *P. aeruginosa* OprI include the B cell epitopes at amino acids 7 to 20 or amino acids 21 to 57 (numbering with respect to the mature *P. aeruginosa* OprI protein; see, Finke et al., (1991) *Infect. Immun.* 59:1251-1254).

In particular embodiments, the *P. aeruginosa* OprI antigen comprises, consists essentially of or consists of one or more, two or more, three or more, or four or more epitopes (e.g., B cell epitopes and/or T cell epitopes), which may include one or more of the epitopes specifically described herein or orthologs or active fragments thereof. In embodiments of the invention, the *P. aeruginosa* OprI antigen comprises, consists essentially of, or consists of the full-length precursor (amino acids 1 to 83) or mature (amino acids 21 to 83) *P. aeruginosa* OprI protein or, alternatively, an active fragment of either of the foregoing (e.g., at least about 6, 8, 10, 15, 20, 30, 50 or 75 or more contiguous amino acids and/or less than about 75, 50, 30, 20, or 15 contiguous amino acids, including any combination of the foregoing as long as the lower limit is less than the upper limit). In embodiments, the *P. aeruginosa* OprI antigen comprises, consists essentially, or consists of amino acids 7-20 and/or amino acids 21 to 57 of the mature OprI protein (numbering with respect to the mature *P. aeruginosa* OprI protein; see, Finke et al., (1991) *Infect. Immun.* 59:1251-1254; von Specht et al., (1995) *Infection and Immunity* 63:1855-1862; U.S. Pat. No. 6,300,102; Mansouri et al., (2003) *FEMS Immunology and Medical Microbiology* 37:161-166; and Saha et al., (2006) *Vaccine* 24:6240-6249) or orthologs or active fragments thereof.

Multiple *P. aeruginosa* antigens may be provided in the form of a fusion peptide, such as an OprI-OprF fusion peptide or an OprF-OprI fusion peptide (see, e.g., von Specht et al., (1995) *Infection and Immunity* 63:1855-1862; U.S. Pat. No. 6,300,102; Mansouri et al., (2003) *FEMS Immunology and Medical Microbiology* 37:161-166; Saha et al., (2006) *Vaccine* 24:6240-6249; and Mansouri et al., (1999) *Infect. Immun.* 67:1461-1470). *P. aeruginosa* OprF and OprI antigens are described in more detail above. Where two antigens are joined as a fusion peptide, they may be joined directly to one another or joined by an intervening amino acid sequence such as a peptide linking or "hinge" segment (e.g., a segment of 1, 2, 3, 4, 6, 8, 10, 15, 20, 30, 50 or more amino acids) and/or another antigen, but generally without any intervening flagellin sequences. Nonlimiting examples of fusion peptides comprise, consist essentially of, or consist of amino acids 190 to 342, amino acids 190 to 350, amino acids 311 to 341, or amino acids 329 to 342 of the *P. aeruginosa* OprF protein and the precursor (amino acids 1-83) or the mature (amino acids 21 to 83) *P. aeruginosa* OprI protein, with or without intervening sequences (as described above), or orthologs or active fragments thereof. In particular embodiments, the *P. aeruginosa* OprI antigen is fused with its amino terminal end to the carboxy terminal end of the *P. aeruginosa* OprF antigen (e.g., OprF-OprI), with or without intervening sequences (as described above). In other embodiments, the *P. aeruginosa* OprF antigen is fused with its amino terminal end to the carboxy terminal end of the *P. aeruginosa* OprI antigen (e.g., OprI-OprF), with or without intervening sequences.

Other suitable OprI and OprF antigens, including fusion peptides thereof, in addition to the antigens specifically disclosed here can be readily identified by those skilled in the art without departing from the present invention.

II. Flagellins.

The inventors have determined that flagellin can function as an adjuvant to enhance the active immune response mounted by a host to a *P. aeruginosa* antigen. Further, when one or more *P. aeruginosa* antigens is presented as a fusion protein with a flagellin adjuvant(s), a synergistic and comprehensive protective immune response, including cellular and humoral immunity as well as a potent antibody-dependent complement-mediated cytotoxicity, can be elicited in the host against *P. aeruginosa* (e.g., motile, nonmucoid *P. aeruginosa*).

Flagellin proteins are known and described, for example, in U.S. Pat. Nos. 6,585,980, 6,130,082; 5,888,810; 5,618,533; 4,886,748 and U.S. Patent Publication No. US 2003/0044429 A1; and Donnelly et al., (2002) *J. Biol. Chem.* 43: 40456. Most gram-negative bacteria express flagella, which are surface structures that provide motility. The flagella are formed from a basal body, a filament, and a hook that connects the two. The filament is formed of a long polymer of a single protein, flagellin, with a small cap protein at the end. Polymerization of flagellin is mediated by conserved regions at the N- and C-termini, whereas the intervening hypervariable region of the flagellin protein is very diverse in sequence and length among species.

The flagellin can be from any suitable source. A number of flagellin genes have been cloned and sequenced (see, e.g., Kuwajima et al., (1986) *J. Bact.* 168:1479; Wei et al., (1985) *J. Mol. Biol.* 186:791-803; and Gill et al., (1983) *J. Biol. Chem.* 258:7395-7401). Non-limiting sources of flagellins include but are not limited to *S. enteritidis, S. typhimurium, S. dublin, H. pylori, V. cholera, S. marcesens, S. flexneri, S. enterica, T. pallidum, L. pneumophila, B. burgdorferei, C. difficile, A. tumefaciens, R. meliloti, B. clarridgeiae, R. lupine, P. mirabilis, B. subtilis, P. aeruginosa,* and *E. coli.* In representative embodiments, the flagellin is a P. auruginosa flagellin (including modified forms thereof). The two most common types of P. auruginosa flagellin are type A and type B, but the P. auruginosa flagellin can be any other flagellin type now known or later discovered. Suitable examples include the type A flagellin sequence from *P. aeruginosa* strain PAK (GenBank Accession No. M57501.1) and the type B flagellin sequence from *P. aeruginosa* strain PAO1 (NCBI Accession No. NC_002516.2).

The N-terminal and C-terminal constant regions of flagellin are well characterized in the art and have been described, for example, in Mimori-Kiyosue et al., (1997) *J. Mol. Virol.* 270:222-237; Iino et al., (1977) Ann. Rev. Genet. 11:161-182; and Schoenhals et al, (1993) *J. Bacteriol.* 175:5395-5402. As is understood by those skilled in the art, the size of the constant regions will vary somewhat depending on the source of the flagellin protein. In general, the N-terminal constant domain includes the approximately 170 or 180 N-terminal amino acids of the protein, whereas the C-terminal constant domain typically spans the approximately 85 to 100 C-terminal amino acids. The central hypervariable region varies considerably by size and sequence among bacteria, and accounts for most of the difference in molecular mass. The N- and C-terminal constant regions of flagellin proteins from a variety of bacteria are known, and others can be readily identified by those skilled in the art using known alignment techniques, which are facilitated by the elucidation of the crystal structure of the flagellin monomer (Samatey et al., (2001) *Nature* 41:331; see also the mapping of the N- and C-terminal constant domains and the hypervariable domains for the *P. aeruginosa* type A [strain PAK] and Type B [strain PAO1] flagellins in Table 1).

The terms "flagellin," "flagellin N-terminal constant region" and "flagellin C-terminal constant region" include active fragments and modifications of any of the foregoing, for example, modifications that enhance the immune response to the *P. aeruginosa* antigen (e.g., by activating the TLR5 pathway). To illustrate, the native flagellin or flagellin regions can be modified to increase safety and/or immune response and/or as a result of cloning procedures or other laboratory manipulations. In some embodiments, the flagellin comprises the full-length flagellin or, alternatively, can comprise an active fragment thereof. Further, the terms "flagellin," "flagellin N-terminal constant region" and "flagellin C-terminal constant region" and like terms include polypeptides that comprise, consist essentially of, or consist of the naturally occurring amino acid sequences and further encompass polypeptides that comprise, consist essentially of, or consist of an amino acid sequence that is substantially identical or similar to the amino acid sequence of a naturally occurring flagellin, flagellin N-terminal constant region or flagellin C-terminal constant region (e.g., type A or type B *P. aeruginosa* flagellin), respectively, or an active fragment thereof As used herein, an "active fragment" of a flagellin, flagellin N-terminal constant region, C-terminal constant region, or any other flagellin region is a fragment of at least about 50, 75, 100, 125, 150, 200, 250 or 300 or more contiguous amino acids and/or less than about 300, 250, 200, 150, 125, 100 or 75 contiguous amino acids, including any combination thereof as long as the lower limit is less than the upper limit, where the active fragment enhances the immune response (optionally, a protective immune response) to the P. aeruginosa antigen(s) in a host (e.g., by activating the TLR5 pathway). In particular embodiments, the active fragment enhances the immune response (optionally a protective immune response) to the P. aeruginosa antigen(s) at least about 25%, 50%, 75%, 80%, 85%, 90%, or 95% or more of the level observed with the full-length flagellin or flagellin region, or enhances the immune response to the same or essentially the same extent as the full-length flagellin or flagellin region or enhances the immune response to an even greater extent than the full-length flagellin or flagellin region. Methods of measuring the immune response are well-known in the art (e.g., measurement of antigen-specific IgG). Further, in embodiments of the invention an "active fragment" of a flagellin, flagellin N-terminal constant region, C-terminal constant region, or any other flagellin domain induces an immune response (optionally a protective immune response) in a host against P. aeruginosa (e.g., IgG that react with the native P. aeruginosa flagellin), that is at least about 25%, 50%, 75%, 80%, 85%, 90%, or 95% or more of the immune response induced by the full-length flagellin or flagellin region, or induces an immune response that is the same as or essentially the same as the full-length flagellin or flagellin region or induces an immune response that is even greater than the immune response induced by the full-length flagellin or flagellin region.

In embodiments of the invention, a "modified" flagellin, flagellin N-terminal constant region, C-terminal constant region, or any other flagellin region (and similar terms) enhances the immune response (optionally a protective immune response) to the P. aeruginosa antigen(s) to at least about 50%, 75%, 80%, 85%, 90%, or 95% or more of the level of enhancement observed with the native flagellin or flagellin region, or enhances the immune response to the same or essentially the same extent as the native flagellin or flagellin region or enhances the immune response to an even greater extent than the native flagellin or flagellin region. Methods of measuring the immune response are well-known in the art (e.g., measurement of antigen-specific IgG). Further, in embodiments of the invention a "modified" flagellin, flagellin N-terminal constant region, C-terminal constant region, or any other flagellin region induces an immune response (optionally a protective immune response) in a host against P. aeruginosa (e.g., IgG that react with the native P. aeruginosa flagellin), that is at least about 25%, 50%, 75%, 80%, 85%, 90%, or 95% or more of the immune response induced by the native flagellin or flagellin region, or induces an immune response that is the same as or essentially the same as the native flagellin or flagellin region or induces an immune response that is even greater than the immune response induced by the native flagellin or flagellin region.

A great deal of structure/function characterization of flagellin proteins has been reported in the literature. Those skilled in the art will be able to identify other suitable flagellin adjuvants within the scope of the present invention, in addition to those specifically disclosed herein, using no more than routine skill. For example, the circulating IgG titers against an antigen following administration of a flagellin fusion protein or flagellin composition (i.e., flagellin+antigen) of the invention can be compared with the circulating IgG induced by administration of the antigen alone.

Generally, the flagellin N-terminal and/or C-terminal constant region comprises a TLR5 recognition site(s) and is able to activate the TLR5 pathway. Regions of the flagellin protein involved in TLR5 signaling have been identified by Smith et al. (2003) Nat. Immunol. 4:1247-1253 (e.g., amino acids 78-129, 135-173 and 394-444 of S. typhimurium flagellin or orthologs or modified forms thereof). Further, in representative embodiments, the N-terminal constant region comprises the N-terminal RINSA domain (amino acids 31-52 of the S. dublin flagellin) as described by Eaves-Pyles et al. (2001) J. Immunology 167: 7009-7016, or an ortholog or modified form thereof that enhances the immunogenicity of the P. aeruginosa antigen.

In further embodiments of the invention, the N-terminal constant region comprises the D1 and D2 domains, and the C-terminal constant region comprises the D1 and D2 domains (Eaves-Pyles et al. (2001) J. Immunology 167: 7009-7016) or a modified form thereof.

In still further embodiments, the flagellin N-terminal and/or C-terminal constant region comprises the peptide GAVQNRFNSAIT (SEQ ID NO:4) as described by U.S. Patent Publication No. US 2003/0044429 A1 to Alderem et al., or an ortholog or modification thereof.

In representative embodiments of the invention, the N-terminal constant domain comprises the "motif N" (e.g., amino acids 98-108 of the S. muenchen flagellin) and/or the C-terminal constant domain comprises the "motif C" (e.g., amino acids 441-449 of S. muenchen flagellin) identified by Kanneganti et al., (2004) J. Biol. Chem. 279:5667-5676, or an ortholog or modified form thereof that enhances an immune response to the P. aeruginosa antigen.

In other illustrative embodiments, the N-terminal constant domain comprises amino acids 88 to 97 of the P. aeruginosa flagellin (see, e.g., Verma et al., (2005) Infect. Immun. 73:8237-8246) or an ortholog or modified form thereof.

In other embodiments, the flagellin adjuvant comprises, consists essentially of or consists of amino acids 1-156 of the Pa01 strain of P. aeruginosa or an ortholog or modified form thereof (see, e.g., Neville et al., (2005) International J. Molecular Medicine 16:165-171).

In some embodiments of the invention, the flagellin hypervariable region between the constant regions is deleted (in whole or in part); in other embodiments the hypervariable region is present.

Further, the flagellin adjuvant can comprise a hinge region between the N-terminal constant and C-terminal constant regions. The hypervariable region or a P. aeruginosa antigen(s) can function as a hinge region. Additionally, or alternatively, a segment of about 2, 3, 4, 6, 8, 10, 15, 20, 30, 50 or more amino acids can function as a hinge region.

Optionally, the flagellin adjuvant can be a fusion protein comprising any other polypeptide of interest. For example, the flagellin adjuvant can be a fusion protein comprising one or more P. aeruginosa antigens and/or one or more antigens from another organism(s) (e.g., bacterial, viral, protozoan, yeast or fungal). Additional P. aeruginosa antigens include without limitation outer membrane protein (e.g., OprF, OprI and/or OprH2) antigens, PilA antigens and/or PcrV antigens.

Further, in representative embodiments, the flagellin adjuvant can be a fusion protein comprising an immunomodulatory compound. For example, it is known in the art that immune responses can be enhanced by an immunomodulatory cytokine or chemokine (e.g., α-interferon, β-interferon, γ-interferon, ω-interferon, τ-interferon, interleukin-1α, interleukin-β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell growth factor, CD40 Ligand, tumor necrosis factor-α, tumor necrosis factor-β, monocyte chemoattractant protein-1, granulocyte-macrophage colony stimulating factor, lymphotoxin, CCL25 [MECK], and CCL28 [TECH]) or active fragments thereof.

III. Flagellin Compositions and Flagellin Fusion Proteins.

The invention further provides compositions comprising one or more flagellin adjuvants and one or more *P. aeruginosa* antigens. In illustrative embodiments of the invention, a fusion protein is provided comprising a flagellin adjuvant and one or more *P. aeruginosa* antigens. Alternatively (or additionally), a flagellin adjuvant and a *P. aeruginosa* antigen can be provided as separate polypeptides, in the same or separate compositions. Flagellin adjuvants and *P. aeruginosa* antigens are as described herein. Further, each component of the composition or fusion protein can be present in multiple copies (e.g., two or more).

In illustrative embodiments, the invention provides a fusion protein comprising: (a) a *P. aeruginosa* type A flagellin adjuvant and/or a *P. aeruginosa* type B flagellin adjuvant; and (b) a *P. aeruginosa* OprI antigen and/or a *P. aeruginosa* OprF antigen.

In representative embodiments, a fusion protein is provided comprising (a) a *P. aeruginosa* type A flagellin adjuvant and a *P. aeruginosa* type 13 flagellin adjuvant; and (b) a *P. aeruginosa* OprI antigen or a *P. aeruginosa* OprF antigen.

In representative embodiments, a fusion peptide is provided comprising a (a) a *P. aeruginosa* type A flagellin adjuvant and a *P. aeruginosa* type B flagellin adjuvant; and (b) a *P. aeruginosa* OprI antigen and a *P. aeruginosa* OprF antigen.

In exemplary embodiments, the invention provides a fusion protein comprising: (a) a *P. aeruginosa* type A flagellin adjuvant; and (b) a *P. aeruginosa* OprI antigen.

In embodiments, the invention provides a fusion protein comprising: (a) a *P. aeruginosa* type B flagellin adjuvant; and (b) a *P. aeruginosa* OprI antigen.

In embodiments, the invention provides a fusion protein comprising: (a) a *P. aeruginosa* type A flagellin adjuvant; and (b) a *P. aeruginosa* OprF antigen.

In embodiments, the invention provides a fusion protein comprising: (a) a *P. aeruginosa* type B flagellin adjuvant; and (b) a *P. aeruginosa* OprF antigen.

In further embodiments, the invention provides a fusion protein comprising: (a) a *P. aeruginosa* type A flagellin adjuvant; and (b) a *P. aeruginosa* OprI antigen and a *P. aeruginosa* OprF antigen. Optionally, the fusion protein comprises a fusion peptide comprising a *P. aeruginosa* OprI antigen and a *P. aeruginosa* OprF antigen.

In other representative embodiments, the invention provides a fusion protein comprising: (a) a *P. aeruginosa* type B flagellin adjuvant; and (b) a *P. aeruginosa* OprI antigen and a *P. aeruginosa* OprF antigen. Optionally, the fusion protein comprises a fusion peptide comprising a *P. aeruginosa* OprI antigen and a *P. aeruginosa* OprF antigen.

The fusion protein can further comprise one or more additional flagellin adjuvants, *P. aeruginosa* antigens, and/or antigens from another organism (e.g., bacterial, viral, protozoan, yeast or fungal).

The *P. aeruginosa* Psl polysaccharide is a galactose- and mannose-rich exopolysaccharide that is implicated in biofilm formation. In embodiments of the invention, the fusion protein further comprises *P. aeruginosa* Psi polysaccharide (e.g., by conjugation). For example, monomers and/or dimers of the *P. aeruginosa* polysaccharide can be conjugated to one or more of the fusion proteins. Methods of conjugating polypeptides and polysaccharides are well-known in the art. In embodiments of the invention, the polysaccharide is conjugated via a linker.

Accordingly, the invention also provides a flagellin adjuvant (e.g., a *P. aeruginosa* type A or type B flagellin adjuvant) or fusion protein of the invention conjugated to *P. aeruginosa* Psl polysaccharide (e.g., Psi monomers and/or dimers).

The conjugates can be prepared with any suitable ratio of the polypeptide to the polysaccharide, which may be optimized to enhance the immunogenicity of the antigen and/or the adjuvant activity of the polypeptide. In representative embodiments, a ratio of polysaccharide to polypeptide (w/w) of greater than about 1:1 is used. In other embodiments, a ratio of polysaccharide to polypeptide of less than about 1:1 is used. In still other embodiments, a ratio of polysaccharide to polypeptide of about 1:1 is used. In representative embodiments, conjugates with a polysaccharide to polypeptide ratio (w/w) of between about 1:2, 1:3, 1:5, 1:10 or 1:15 (excess polypeptide) and about 2:1, 3:1, 5:1, 10:1 or 15:1 (excess polysaccharide) are used.

Further, in embodiments of the invention, the polysaccharide is covalently linked to the N-terminus and/or C-terminus of the flagellin adjuvant or fusion protein.

The invention also provides a composition comprising one or more flagellin adjuvants and one or more *P. aeruginosa* antigens of the invention. As described further above, the flagellin adjuvant(s) can be coupled (i.e., fused) to the *P. aeruginosa* antigen(s) to form a fusion protein. In other embodiments, the flagellin adjuvant(s) is not fused to the *P. aeruginosa* antigen(s).

Accordingly, in representative embodiments, the invention provides a composition comprising one or more fusion proteins comprising a flagellin adjuvant(s) and a *P. aeruginosa* antigen(s) as described above. As one non-limiting example, in embodiments the invention provides a composition comprising: (a) a fusion protein comprising (i) a *Pseudomonas aeruginosa* type A flagellin adjuvant; and (ii) at least one *Pseudomonas aeruginosa* antigen; and (b) a fusion protein comprising (i) a *Pseudomonas aeruginosa* type B flagellin adjuvant; and (ii) at least one *Pseudomonas aeruginosa* antigen.

In exemplary embodiments, the invention provides a composition comprising: (a) a fusion protein comprising (i) a *P. aeruginosa* type A flagellin adjuvant; and (ii) a *P. aeruginosa* OprI antigen; and (b) a fusion protein comprising (i) a *P. aeruginosa* type B flagellin adjuvant; and (ii) a *Pseudomonas aeruginosa* OprF antigen.

In representative embodiments, the invention provides a composition comprising: (a) a fusion protein comprising (i) a *P. aeruginosa* type A flagellin adjuvant; and (ii) a *P. aeruginosa* OprF antigen; and (b) a fusion protein comprising (i) a *P. aeruginosa* type B flagellin adjuvant; and (ii) a *Pseudomonas aeruginosa* OprI antigen.

In embodiments, the invention provides a composition comprising: (a) a fusion protein comprising (i) a *P. aeruginosa* type A flagellin adjuvant; and (ii) a *P. aeruginosa* OprF antigen and/or a *P. aeruginosa* OprI antigen; and (b) a fusion protein comprising (i) a *P. aeruginosa* type B flagellin adjuvant; and (ii) a *P. aeruginosa* OprF antigen and/or a *P. aeruginosa* OprI antigen. Optionally, one or more of the fusion proteins comprises a fusion peptide comprising a *P. aeruginosa* OprI antigen and a *P. aeruginosa* OprF antigen.

In embodiments, the invention provides a composition comprising: (a) a fusion protein comprising (i) a *P. aeruginosa* type A flagellin adjuvant; and (ii) a *P. aeruginosa* OprF antigen and a *P. aeruginosa* OprI antigen; and (b) a fusion protein comprising (i) a *P. aeruginosa* type B flagellin adjuvant; and (ii) a *P. aeruginosa* OprF antigen and a *P. aeruginosa* OprI antigen. Optionally, one or more of the fusion proteins comprises a fusion peptide comprising a *P. aeruginosa* OprI antigen and a *P. aeruginosa* OprF antigen.

The composition can further comprise one or more additional flagellin adjuvants, *P. aeruginosa* antigens, and/or antigens from another organism (e.g., bacterial, viral, protozoan, yeast or fungal), which may or may not be fused to a flagellin adjuvant.

The composition can further comprise *P. aeruginosa* Psl polysaccharide, which can be present as free polysaccharide and/or conjugated to a carrier (e.g., a carrier protein). Optionally, the *P. aeruginosa* Psl polysaccharide is conjugated to a flagellin adjuvant and/or fusion protein of the invention. For example, monomers and/or dimers of the *P. aeruginosa* polysaccharide can be conjugated to one or more flagellin adjuvants and/or fusion proteins of the invention. Psi and Psi conjugates are discussed in more detail above.

The *P. aeruginosa* antigen(s) can be fused to the flagellin adjuvant in any suitable configuration, with or without intervening sequences. For example, one or more of the *P. aeruginosa* antigen(s) can be an N-terminal extension of the flagellin adjuvant. As another option, one or more of the *P. aeruginosa* antigen(s) can be a C-terminal extension of the flagellin adjuvant. Further, one or more of the *P. aeruginosa* antigen(s) can be inserted into the flagellin adjuvant (e.g., between the N-terminal and C-terminal constant regions). If multiple *P. aeruginosa* antigens are present, they can be incorporated into different sites in the fusion protein. For example, one antigen can be an N-terminal extension and one can be inserted into the protein sequence of the flagellin adjuvant (e.g., between the N-terminal and C-terminal constant regions). As another nonlimiting example, one antigen can be a C-terminal extension and one can be inserted into the protein sequence of the flagellin adjuvant (e.g., between the N-terminal and C-terminal constant regions). As yet another option, one antigen can be an N-terminal extension and the other can be a C-terminal extension. In embodiments of the invention, a fusion peptide comprising two or more *P. aeruginosa* antigens (e.g., an OprF-OprI fusion peptide in which the carboxy terminus of the OprF antigen is fused to the N-terminus of the OprI antigen) is incorporated as an N-terminal extension, a C-terminal extension and/or can be inserted into the protein coding sequence of the flagellin adjuvant (e.g., between the N-terminal and C-terminal constant regions). Further, when there are multiple flagellin adjuvants, the antigen(s) need not be positioned in the same location in each of the flagellin adjuvants.

In embodiments wherein the *P. aeruginosa* antigen(s) is located between the N-terminal constant region and the C-terminal constant region of the flagellin adjuvant, the *P. aeruginosa* antigen(s) can further be located between the N-terminal constant region and the hypervariable region and/or between the hypervariable region and the C-terminal constant region and/or inserted into the hypervariable region. Further, the hypervariable region can be partially or completely deleted. When the antigen(s) is positioned between one of the constant regions and the hypervariable region or is inserted into the hypervariable region, the sequences need not be directly fused to each other, i.e., there may be an intervening sequence.

As described above, the flagellin adjuvant can comprise a hinge region between the N-terminal constant and C-terminal constant regions. The hypervariable region and/or the *P. aeruginosa* antigen(s) can function as a hinge region. Additionally, or alternatively, a segment of about 1, 2, 3, 4, 6, 8, 10, 15, 20, 30, 50 or more amino acids can function as a hinge region.

Non-limiting examples of fusion proteins of the invention are provided in the working Examples herein. Additional fusion proteins beyond those specifically disclosed herein can be routinely identified by those skilled in the art.

Unless indicated otherwise, flagellin and flagellin fusion proteins of the invention are administered per se as a polypeptide (or a nucleic acid encoding the polypeptide) and not as part of a live, killed, or recombinant bacterium- or virus-vectored vaccine. Further, unless indicated otherwise, the flagellins and flagellin fusion proteins of the invention are isolated flagellins and flagellin fusion proteins, e.g., are not incorporated into flagella.

IV. Recombinant Nucleic Acids and Production of Fusion Proteins.

Except as otherwise indicated, standard methods known to those skilled in the art may be used for cloning genes, amplifying and detecting nucleic acids, generating fusion constructs, expressing peptides in host cells or organisms, and the like. Such techniques are known to those skilled in the art. See, e.g., Sambrook et al., "Molecular Cloning" A Laboratory Manual 2nd Ed. (Cold Spring Harbor, N.Y., 1989); F. M. Ausubel et al. Current Protocols in Molecular Biology (Green Publishing Associates, Inc. and John Wiley & Sons, Inc., New York).

As used herein, the term "nucleic acid" encompasses both RNA and DNA, including cDNA, genomic DNA, synthetic (e.g., chemically synthesized) DNA and chimeras of RNA and DNA. The nucleic acid may be double-stranded or single-stranded. The nucleic acid may be synthesized using nucleotide analogs or derivatives (e.g., inosine or phosphorothioate nucleotides). Such nucleotides can be used, for example, to prepare nucleic acids that have altered base-pairing abilities or increased resistance to nucleases.

The fusion proteins of the invention can be produced in, and optionally purified from, cultured cells or organisms expressing a heterologous nucleic acid encoding the fusion protein for a variety of purposes (e.g., to produce immunogenic formulations, as a diagnostic or research reagent, and the like).

In some embodiments, the fusion protein can be collected and, optionally, purified from the host cell. For example, the fusion protein can be collected from the conditioned medium. According to this embodiment, it may be advantageous to express the fusion protein operably associated with a secretory signal sequence. Alternatively, the fusion protein can be isolated from the host cell (e.g., the host cell can be lysed and the fusion protein isolated therefrom).

In other embodiments, the host cells are collected and the fusion protein is not isolated therefrom.

Unless indicated otherwise, the flagellins and fusion proteins of the invention are not expressed as part of flagella (i.e., are not incorporated into flagella).

Generally, the heterologous nucleic acid is incorporated into an expression vector (viral or non-viral). Suitable expression vectors include but are not limited to plasmids, bacteriophage, bacterial artificial chromosomes (bacs), yeast artificial chromosomes (yacs), cosmids, virus vectors, and the like. Expression vectors compatible with various host cells are well known in the art and contain suitable elements for transcription and translation of nucleic acids. Typically, an expression vector contains an "expression cassette," which includes, in the 5' to 3' direction, a promoter, a coding sequence encoding the fusion protein operatively associated with the promoter, and, optionally, a termination sequence including a stop signal for RNA polymerase and a polyadenylation signal for polyadenylase.

Expression vectors can be designed for expression of polypeptides in prokaryotic or eukaryotic cells. For example, polypeptides can be expressed in bacterial cells such as *E. coli*, insect cells (e.g., in the baculovirus expression system), yeast cells, mammalian cells, or plant cells. Examples of vectors for expression in yeast *S. cerevisiae* include pYepSecl (Baldari et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.). Baculovirus vectors available for expression of nucleic acids to produce proteins in cultured insect cells (e.g., Sf9 cells) include the pAc series (Smith et al., (1983) *Mol. Cell. Biol.* 3:2156-2165) and the pVL series (Lucklow, V. A., and Summers, M.d. (1989) *Virology* 170:31-39).

Additionally, the expression vector will generally include expression control sequences (e.g., transcription/translation control signals and polyadenylation signals), which are operably associated with the nucleic acid sequence encoding the fusion protein of the invention. It will be appreciated that a variety of promoter/enhancer elements can be used depending on the level and tissue-specific expression desired. The promoter can be constitutive or inducible (e.g., the metallothionein promoter or a hormone inducible promoter), depending on the pattern of expression desired. The promoter can be native or foreign and can be a natural or a partially or completely synthetic sequence. By foreign, it is intended that the promoter is not naturally occurring in the host cell into which the nucleic acid is introduced. The promoter is chosen so that it will function in the target cell(s) of interest. Moreover, specific initiation signals are generally provided for efficient translation of inserted protein coding sequences. These translational control sequences, which can include the ATG initiation codon and adjacent sequences, can be of a variety of origins, both natural and synthetic. In embodiments of the invention wherein the expression vector comprises two open reading frames to be transcribed, the open reading frames can be operatively associated with separate promoters or with a single upstream promoter and one or more downstream internal ribosome entry site (IRES) sequences (e.g., the picornavirus EMC IRES sequence).

Examples of mammalian expression vectors include pCDM8 (Seed, (1987) *Nature* 329:840) and pMT2PC (Kaufman et al. (1987), *EMBO J.* 6:187-195). When used in mammalian cells, the expression vector's control functions are often provided by viral regulatory elements. For example, commonly used promoters are derived from polyoma, adenovirus 2, cytomegalovirus and Simian Virus 40.

The invention further provides a host cell comprising (transiently or stably) a nucleic acid encoding a fusion protein of the invention. Suitable host cells are well-known in the art and include prokaryotic and eukaryotic cells. See, e.g., Goeddel, Gene Expression Technology: *Methods in Enzymology* 185, Academic Press, San Diego, Calif. (1990). It is well-known that proteins can be expressed in bacterial cells such as *E. coli*, insect cells (e.g., Sf9 cells), yeast cells, plant cells or mammalian cells (e.g., human, rat, mouse, hamster, bovine, porcine, ovine, caprine, equine, feline, canine, lagomorph, simian and the like). The host cell can be a cultured cell such as a cell of a primary or immortalized cell line. The host cell can be a cell in a microorganism, animal or plant being used essentially as a bioreactor. In particular embodiments of the present invention, the host cell is an insect cell that allows for replication of expression vectors. For example, the host cell can be from *Spodoptera frugiperda*, such as the Sf9 or Sf21 cell lines, *Drosophila* cell lines, or mosquito cell lines, e.g., *Aedes albopictus* derived cell lines. Use of insect cells for expression of heterologous proteins is well documented, as are methods of introducing nucleic acids, such as vectors, e.g., insect-cell compatible vectors (such as baculovirus vectors), into such cells and methods of maintaining such cells in culture. See, for example, Methods in Molecular Biology, ed. Richard, Humana Press, NJ (1995); O'Reilly et al., Baculovirus Expression Vectors, A Laboratory Manual, Oxford Univ. Press (1994); Samulski et al., *J. Virol.* 63:3822-8 (1989); Kajigaya et al., *Proc. Nat'l. Acad. Sci. USA* 88: 4646-50 (1991); Ruffing et al., *J. Virol.* 66:6922-30 (1992); Kimbauer et al., *Virology* 219:37-44 (1996); Zhao et al., *Virology* 272: 382-93 (2000); and U.S. Pat. No. 6,204,059 to Samulski et al. In particular embodiments of the present invention, the insect cell is an Sf9 cell.

Vectors can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA) into a host cell, including calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al. (Molecular Cloning: A Laboratory Manual, 2nd Edition, Cold Spring Harbor Laboratory press (1989)), and other laboratory manuals.

In further embodiments of the present invention, the host cell can be stably transformed with the heterologous nucleic acid sequence encoding the fusion protein. "Stable transformation" as used herein generally refers to the integration of the heterologous nucleic acid sequences into the genome of the host cell in contrast to "transient transformation" wherein the heterologous nucleic acid sequence introduced into the host cell does not integrate into the genome of the host cell. The term "stable transformant" can further refer to stable maintenance of an episome (e.g., an Epstein-Barr Virus (EBV) derived episome) in the cell.

When producing stably transformed cells, often only a small fraction of cells (in particular, mammalian cells) integrate a foreign nucleic acid into their genome. In order to identify and select these integrants, a nucleic acid that encodes a selectable marker (e.g., resistance to antibiotics) can be introduced into the host cells along with the nucleic acid of interest. Preferred selectable markers include those that confer resistance to drugs, such as G418, hygromycin and methotrexate. Nucleic acids encoding a selectable marker can be introduced into a host cell on the same vector as that comprising the nucleic acid of interest or can be introduced on a separate vector. Cells stably transfected with the introduced nucleic acid can be identified by drug selection (e.g., cells that have incorporated the selectable marker gene will survive, while the other cells die).

The fusion protein can also be produced in a transgenic plant in which the isolated nucleic acid encoding the fusion protein is inserted into the nuclear or plastidic genome or is maintained as a stable episomal element. Plant transformation is known as the art. See, in general, Methods in Enzymology Vol. 153 ("Recombinant DNA Part D") 1987, Wu and Grossman Eds., Academic Press and European Patent Application EP 0 693 554.

Foreign nucleic acids can be introduced into plant cells or protoplasts by several methods. For example, nucleic acid can be mechanically transferred by microinjection directly into plant cells by use of micropipettes. Foreign nucleic acid can also be transferred into a plant cell by using polyethylene glycol which forms a precipitation complex with the genetic material that is taken up by the cell (Paszkowski et al. (1984) *EMBO J.* 3:2712-22). Foreign nucleic acid can be introduced into a plant cell by electroporation (Fromm et al. (1985) *Proc. Natl. Acad. Sci. USA* 82:5824). In this technique, plant protoplasts are electroporated in the presence of plasmids or nucleic acids containing the relevant genetic construct. Electrical impulses of high field strength reversibly permeabilize biomembranes allowing the introduction of the plasmids. Electroporated plant protoplasts reform the cell wall, divide, and form a plant callus. Selection of the transformed plant cells comprising the foreign nucleic acid can be accomplished using phenotypic markers.

Cauliflower mosaic virus (CaMV) can be used as a vector for introducing foreign nucleic acids into plant cells (Hohn et al. (1982) "Molecular Biology of Plant Tumors," Academic Press, New York, pp. 549-560; Howell, U.S. Pat. No. 4,407,956). CaMV viral DNA genome is inserted into a parent bacterial plasmid creating a recombinant DNA molecule which can be propagated in bacteria. The recombinant plasmid can be further modified by introduction of the desired DNA sequence. The modified viral portion of the recombinant plasmid is then excised from the parent bacterial plasmid, and used to inoculate the plant cells or plants.

High velocity ballistic penetration by small particles can be used to introduce foreign nucleic acid into plant cells. Nucleic acid is disposed within the matrix of small beads or particles, or on the surface (Klein et al. (1987) *Nature* 327:70-73).

A nucleic acid can be introduced into a plant cell by infection of a plant cell with *Agrobacterium tumefaciens* or *Agrobacterium rhizogenes* transformed with the nucleic acid. Under appropriate conditions, the transformed plant cells are grown to form shoots, roots, and develop further into plants. The nucleic acids can be introduced into plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al., (1987) *Science* 227:1229-1231; Fraley et al. (1983) *Proc. Natl. Acad. Sci. USA* 80:4803).

The fusion protein can further comprise other polypeptides, for example, purification signals (such as poly-His, a FLAG epitope, c-myc, hemagglutinin and the like), detectable signals (e.g., such as a reporter protein including without limitation alkaline phosphatase, green fluorescent protein, glutathione-S-transferase, β-glucuronidase, β-galactosidase, luciferase, etc.) or other polypeptides (e.g., cytokines or other antigens from *P. aeruginosa* or other organisms).

V. Methods of Administration and Subjects.

The present invention can be practiced for prophylactic and/or therapeutic purposes, in accordance with known techniques (see, e.g., PCT Application WO 2004/101737 to Pizzo et al.).

The invention can be practiced to produce an immune response against *P. aeruginosa* in a subject, optionally a protective immune response. With respect to a protective immune response, the present invention can be practiced prophylactically to prevent infection by *P. aeruginosa*. In other embodiments, the methods of the invention are practiced to treat a subject infected by *P. aeruginosa*. The *P. aeruginosa* infection can be an infection with nonmucoid or mucoid *P. aeruginosa*. In embodiments of the invention, the *P. aeruginosa* infection is a nonmucoid, motile (i.e., comprising flagella) *P. aeruginosa* infection.

Immunogenic formulations for use in the inventive methods are described below. Boosting dosages can further be administered over a time course of days, weeks, months or years. In chronic infection, initial high doses followed by boosting doses may be advantageous.

By the term "treat," "treating" or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the progression of the disease or disorder.

A "treatment effective" amount as used herein is an amount that is sufficient to treat (as defined herein) the subject. Those skilled in the art will appreciate that the therapeutic effects need not be complete or curative, as long as some benefit is provided to the subject.

The terms "prevent," "preventing" and "prevention of" (and grammatical variations thereof) refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

A "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

The terms "vaccination" or "immunization" are well-understood in the art, and are used interchangeably herein unless otherwise indicated. For example, the terms vaccination or immunization can be understood to be a process that increases an organism's immune response to antigen and therefore to resist or overcome infection. In the case of the present invention, vaccination or immunization against *P. aeruginosa* increases the organism's immune response to resist or overcome infection by *P. aeruginosa*.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, Immunophysiology: Cell Function and Cellular Interactions in Antibody Formation, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

The terms "protective" immune response or "protective" immunity as used herein indicates that the immune response confers some benefit to the subject in that it prevents or reduces the incidence and/or severity and/or duration of disease. Alternatively, a protective immune response or protective immunity may be useful in the therapeutic treatment of existing disease.

Unless indicated otherwise, the terms "protect," "protecting," "protection" and "protective" (and grammatical variations thereof) encompass both methods of preventing and treating *P. aeruginosa* infection in a subject.

The present invention can be practiced for both medical and veterinary purposes. Subjects to be treated by the methods of the invention include both avian and mammalian subjects, mammalian subjects including but not limited to humans, non-human primates (e.g., monkeys, baboons, and chimpanzees), dogs, cats, goats, horses, pigs, cattle, sheep, and the like, and laboratory animals (e.g., rats, mice, gerbils, hamsters, and the like). Suitable subjects include both males and females and subjects of all ages including infant, juvenile, adolescent, adult and geriatric subjects. Subjects may be treated for any purpose, such as for eliciting a protective immune response; for eliciting the production of antibodies in that subject, which antibodies can be collected and used for other purposes such as research or diagnostic purposes or for administering to other subjects to produce passive immunity therein, etc.

In particular embodiments, the subject has or is considered at risk for *P. aeruginosa* infection, for example, a subject with cystic fibrosis, a subject with a burn injury, in an immunocompromised state (e.g., an AIDS patient or cancer patient) and/or a subject on a ventilator.

In particular embodiments, the subject is a pediatric subject with cystic fibrosis, e.g., is less than about 2, 4, 6, 8, 10 or 12 years of age. In other representative embodiments, the subject has cystic fibrosis and is administered a fusion protein, composition or immunogenic formulation of the invention prior to infection with *P. aeruginosa* or within about six months, 1 year, 2 years, 3 years, 4 years, 5 years, 6 years, 8 years or 10 years after diagnosis with CF and/or first *P. aeruginosa* infection. In embodiments of the invention, the subject has cystic fibrosis and is infected with a nonmucoid *P. aeruginosa*, optionally a motile, nonmucoid *P. aeruginosa*. In embodiments, the first administration is prior to the onset of a mucoid *P. aeruginosa* infection, e.g., after infection with nonmucoid *P. aeruginosa*.

In some embodiments the subjects are aged subjects, e.g., human subjects 50 or 60 years old or more, where other adjuvants such as alum are generally less effective.

Accordingly, in particular embodiments, the invention provides a method of producing an immune response against *P. aeruginosa* (mucoid or nonmucoid, including motile nonmucoid) in a subject (e.g., a mammalian subject such as a human subject), the method comprising administering a fusion protein, composition or pharmaceutical formulation of the invention to the mammalian subject in an amount effective to produce an immune response in the subject against *P. aeruginosa*.

The invention also provides a method of preventing *P. aeruginosa* infection (mucoid or nonmucoid, including motile nonmucoid) in a subject (e.g., a mammalian subject such as a human subject), the method comprising administering a fusion protein, composition or immunogenic formulation of the invention to the subject in an amount effective to prevent *Pseudomonas aeruginosa* infection in the subject.

The invention further provides a method of enhancing an immune response (optionally, a protective immune response) to *P. aeruginosa* (mucoid or nonmucoid, including motile nonmucoid) in a subject (e.g., a mammalian subject such as a human subject), the method comprising administering a fusion protein, composition or immunogenic formulation of the invention to the subject in an amount effective to enhance the immune response to *Pseudomonas aeruginosa* in the subject.

The invention also contemplates a method of treating a subject (e.g., a mammalian subject such as a human subject) infected with *P. aeruginosa* (mucoid or nonmucoid, including motile nonmucoid), the method comprising administering a fusion protein, composition or immunogenic formulation of the invention to the subject in an amount effective to treat the *P. aeruginosa* infection in the subject.

The invention further encompasses a method of protecting a subject (e.g., a mammalian subject such as a human) from *P. aeruginosa* infection (mucoid or nonmucoid, including motile nonmucoid), the method comprising administering a fusion protein, composition or immunogenic formulation of the invention to the subject in an amount effective to protect the subject from *P. aeruginosa* infection.

Also provided is a method of treating a subject (e.g., a mammalian subject such as a human) that is infected with a nonmucoid *P. aeruginosa* infection to prevent progression to a mucoid *P. aeruginosa* infection, the method comprising administering a fusion protein, composition or immunogenic formulation of the invention to the subject in an amount effective to protect the subject from *P. aeruginosa* infection.

When not administered in the form of a fusion protein, the flagellin adjuvant(s) and *P. aeruginosa* antigen(s) can be administered in the same or separate compositions. If administered as separate compositions, they can optionally be administered concurrently. As used herein, the term "concurrently" means sufficiently close in time to produce a combined effect (that is, concurrently can be simultaneously, or it can be two or more events occurring within a short time period [e.g., minutes or hours] before or after each other).

Administration can be by any route known in the art. As non-limiting examples, the route of administration can be by inhalation (e.g., oral and/or nasal inhalation), oral, buccal (e.g., sublingual), rectal, vaginal, topical (including administration to the airways), intraocular, transdermal, by parenteral (e.g., intramuscular [e.g., administration to skeletal muscle], intravenous, intra-arterial, intraperitoneal and the like), subcutaneous, intradermal, intrapleural, intracerebral, and intrathecal routes.

In particular embodiments, administration is to a mucosal surface, e.g., by intranasal, inhalation, intra-tracheal, oral, buccal (e.g., sublingual), intra-ocular, rectal or vaginal administration, and the like. In general, mucosal administration refers to delivery to a mucosal surface such as a surface of the respiratory tract, gastrointestinal tract, urinary tract, reproductive tract, etc.

Methods of administration to the respiratory tract include but are not limited to transmucosal, intranasal, inhalation, bronchoscopic administration, or intratracheal administration or administration to the lungs.

The fusion proteins, compositions, and immunogenic formulations of the invention can be administered to the lungs of a subject by any suitable means, optionally by administering an aerosol suspension of respirable particles comprising the fusion protein, composition, or immunogenic formulation which the subject inhales. The respirable particles can be liquid or solid. Aerosols of liquid particles comprising a fusion protein, composition, or immunogenic formulation of the invention may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the can likewise be produced with any solid particulate medicament aerosol generator, by techniques known in the pharmaceutical art.

The polypeptide(s) of the invention can be delivered per se or by delivering nucleic acid(s) that encodes the polypeptide(s) and is expressed in the subject to produce the polypeptide(s), such as described in U.S. Pat. No. 5,589,466 to Felgner et al.

Immunomodulatory compounds, such as immunomodulatory chemokines and cytokines (preferably, CTL inductive cytokines) can be administered concurrently to a subject.

Cytokines may be administered by any method known in the art. Exogenous cytokines may be administered to the subject, or alternatively, a nucleic acid encoding a cytokine may be delivered to the subject using a suitable vector, and the cytokine produced in vivo. In particular embodiments, the cytokine is provided as a part of a fusion protein of the invention. For example, a fusion protein comprising a flagellin adjuvant, a *P. aeruginosa* antigen, and an immunomodulatory cytokine (e.g., interferon-γ) can be administered.

In addition to their use for prophylactic or therapeutic purposes, the fusion proteins, compositions, and immunogenic formulations of the present invention can be administered to subjects for the purpose of producing antibodies to a *P. aeruginosa* antigen (e.g., a flagellin antigen and/or an outer membrane protein antigen), which antibodies are in turn useful for diagnostic or therapeutic/prophylactic purposes in human and animal subjects.

VI. Pharmaceutical Formulations.

The invention further provides pharmaceutical formulations (e.g., immunogenic formulations) comprising a fusion protein or composition of the invention in a pharmaceutically acceptable carrier. In particular embodiments, the pharmaceutical composition is formulated for mucosal delivery. By "pharmaceutically acceptable" it is meant a material that is not toxic or otherwise undesirable.

In representative embodiments, the fusion protein is present in the pharmaceutical composition in an "immunogenically effective" amount. An "immunogenically effective amount" is an amount that is sufficient to evoke an active immune response (i.e., cellular and/or humoral) in the subject to which the pharmaceutical composition is administered, optionally a protective immune response (e.g., a prophylactic and/or therapeutic after onset of infection). The degree of protection conferred need not be complete or permanent, as long as the benefits of administering the pharmaceutical formulation outweigh any disadvantages thereof. Immunogenically effective amounts depend on the fusion protein, the manner of administration, the stage and severity of the disease being treated, the general state of health of the subject, and the judgment of the prescribing physician and can be routinely determined by those skilled in the art.

As described above, unless indicated otherwise, the flagellin and flagellin fusion proteins of the invention are administered per se as a polypeptide(s) (or nucleic acid encoding the polypeptide(s)) and not as part of live, killed, or recombinant bacterium- or virus-vectored vaccine. Further, unless indicated otherwise, the flagellins and flagellin fusion proteins of the invention are isolated flagellins and flagellin fusion proteins, e.g., are not incorporated into flagella.

Dosages of pharmaceutically active compounds can be determined by methods known in the art, see, e.g., Remington's Pharmaceutical Sciences (Maack Publishing Co., Easton, Pa.). In particular embodiments, the dosage of the fusion proteins of the present invention ranges from at least about 0.1, 0.5, 1, 10, 25, 50, 100, 150, 250, 300, 500 or 1000 µg for a typical (e.g., 70 kg) subject. The initial dose can be followed by boosting dosages over weeks, months or years of from about 1 pg to 300, 500 or 1000 µg depending on the subject's response to the initial dosage.

In embodiments of the invention, the fusion protein (flagellin-antigen) is at least about 2-fold, 3-fold, 5-fold, 10-fold, 15-fold, 20-fold, 25-fold or 30-fold more active (e.g., in inducing antigen specific IgG) as the separate polypeptides (e.g., flagellin+antigen). Accordingly, in embodiments, the dosage of the fusion protein is 50% or less, 25% or less, 10% or less, 5% or less, 4% or less, or 3% or less of the dosage of the separate polypeptides to achieve the same immunogenic response against the antigen. Further, the quality of the antibodies produced by the fusion proteins of the invention may be greater than those produced by the separate polypeptides, for example, in terms of IgG isotype and/or affinity of the antibodies for antigen.

Optionally, the fusion protein or composition is present in an immunogenically effective amount, as defined herein. Further, in some embodiments, the flagellin adjuvant is present in an "adjuvant effective amount." An "adjuvant effective amount" is an amount of the flagellin adjuvant that is sufficient to enhance or stimulate the active immune response (cellular and/or humoral, e.g., including antibody-dependent complement mediated cytotoxicity) mounted by the host against the *P. aeruginosa* antigen(s), optionally an active mucosal immune response. In particular embodiments, the active immune response (e.g., humoral and/or cellular immune response, e.g., including antibody-dependent complement mediated cytotoxicity) by the host is enhanced by at least about 2, 3, 4, 5, 10, 15, 20, 30, 40, 50, 60, 75, 100, 150, 500, 1000-fold or more. In other embodiments, an "adjuvant effective amount" is an amount of the flagellin adjuvant that reduces the amount of antigen required to achieve a specified level of immunity (cellular and/or humoral), optionally mucosal immunity, for example, a reduction of at least about 15%, 25%, 35%, 50%, 65%, 75%, 80%, 85%, 90%, 95%, 98% or more in the amount of antigen. As a further option, an "adjuvant effective amount" can refer to an amount of the flagellin adjuvant that accelerates the induction of the immune response in the host and/or reduces the need for booster immunizations to achieve protection. As yet another alternative, an "adjuvant effective amount" can be an amount that prolongs the time period over which an immune response, optionally a protective immune response, is sustained (e.g., by at least about a 2-fold, 3-fold, 5-fold, 10-fold, 20-fold longer time period or more).

Dosages of the flagellin adjuvant and *P. aeruginosa* antigen(s) (if not in the form of a fusion protein) can be determined by those skilled in the art. In particular embodiments, dosages of the flagellin adjuvant are in the range from about 0.1, 0.5, 1, 10, 25, 50, 100 or 150 µg to about 200, 250, 300, 500, 1000, or 2500 µg for a typical (e.g., 70 kg) subject. In particular embodiments, dosages are from about 10 to 1000 µg, or from about 50 to 500 µg, or from about 150 to 300 µg for a typical subject. Suitable dosages of the *P. aeruginosa* antigen(s) can range from about 0.1, 0.5, 1, 10, 25, 50, 100 or 150 µg to about 200, 300, 500, 1000, 1500, 2000, 2500 or 5000 µg for a typical (e.g. 70 kg) subject. In particular embodiments, the dosage of the *P. aeruginosa* antigen is from about 50 to 2000 µg, from about 150 to about 1500 µg, or from about 300 to about 1000 µg for a typical subject. The initial dose can be followed by boosting dosages over weeks, months or years of from about 1 ug to about 1000 µg depending on the subject's response to the initial dosage.

Optionally, the pharmaceutical formulation can comprise one or more additional *P. aeruginosa* antigens, which may or not be present as a fusion protein comprising the antigen(s) and a flagellin adjuvant. Additional *P. aeruginosa* antigens include without limitation Psl polysaccharide antigens, lipopolysaccharide antigens, outer membrane protein antigens (e.g., OprF, OprI and/or OprH2), PilA and/or PcrV. Further, the pharmaceutical formulation can comprise one or more antigens from another organism (e.g., bacterial, viral, protozoan, yeast or fungal), which may or may not be present as a fusion protein comprising the antigen(s) and a flagellin adjuvant.

The pharmaceutical formulations of the invention can optionally comprise other medicinal agents, pharmaceutical agents, stabilizing agents, buffers, carriers, diluents, salts, tonicity adjusting agents, wetting agents, and the like, for example, sodium acetate, sodium lactate, sodium chloride, potassium chloride, calcium chloride, sorbitan monolaurate, triethanolamine oleate, etc.

For injection, the carrier will typically be a liquid. For other methods of administration, the carrier may be either solid or liquid. For inhalation administration, the carrier will be respirable, and is typically in a solid or liquid particulate form.

While adjuvants beyond flagellin are generally not required, the composition can optionally comprise an additional adjuvant, such as complete or incomplete Freund's adjuvant, aluminum phosphate, aluminum hydroxide, alum, cytokines, TLR ligands, and the like.

The concentration of the polypeptide(s) in the pharmaceutical formulations can vary widely, e.g., from less than about 0.01% or 0.1% up to at least about 2% to as much as 20% to 50% or more by weight, and will be selected primarily by fluid volumes, viscosities, etc., in accordance with the particular mode of administration selected.

The polypeptide(s) can be formulated for administration in a pharmaceutical carrier in accordance with known techniques. See, e.g., Remington, The Science And Practice of Pharmacy ($9^{th}$ Ed. 1995). In the manufacture of a pharmaceutical composition according to the invention, the polypeptide(s) (including physiologically acceptable salts thereof) is typically admixed with, inter alia, an acceptable carrier. The carrier can be a solid or a liquid, or both, and is optionally formulated with the compound as a unit-dose formulation, for example, a tablet. A variety of pharmaceutically acceptable aqueous carriers can be used, e.g., water, buffered water, 0.9% saline, 0.3% glycine, hyaluronic acid, pyrogen-free water, pyrogen-free phosphate-buffered saline solution, bacteriostatic water, or Cremophor EL[R] (BASF, Parsippany, N.J.), and the like. These compositions can be sterilized by conventional techniques. One or more fusion proteins can be incorporated in the formulations of the invention, which can be prepared by any of the well-known techniques of pharmacy.

The pharmaceutical formulations can be packaged for use as is, or lyophilized, the lyophilized preparation generally being combined with a sterile aqueous solution prior to administration. The compositions can further be packaged in unit/dose or multi-dose containers, for example, in sealed ampoules and vials.

The pharmaceutical formulations can be formulated for administration by any method known in the art according to conventional techniques of pharmacy. For example, the compositions can be formulated to be administered intranasally, by inhalation (e.g., oral inhalation), orally, buccally (e.g., sublingually), rectally, vaginally, topically, intrathecally, intraocularly, transdermally, by parenteral administration (e.g., intramuscular [e.g., skeletal muscle], intravenous, subcutaneous, intrapleural, intracerebral and intraarterial, intrathecal), or topically (e.g., to both skin and mucosal surfaces, including airway surfaces).

In particular embodiments, the pharmaceutical composition is administered to a mucosal surface, e.g., by intranasal, inhalation, intratracheal, oral, buccal, rectal, vaginal or intraocular administration, and the like.

For intranasal or inhalation administration, the pharmaceutical formulation can be formulated as an aerosol (this term including both liquid and dry powder aerosols). For example, the pharmaceutical formulation can be provided in a finely divided form along with a surfactant and propellant. Typical percentages of the composition are 0.01-20% by weight, preferably 1-10%. The surfactant is generally nontoxic and soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1-20% by weight of the composition, preferably 0.25-5%. The balance of the composition is ordinarily propellant. A carrier can also be included, if desired, as with lecithin for intranasal delivery. Aerosols of liquid particles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles can likewise be produced with any solid particulate medicament aerosol generator, by techniques known in the pharmaceutical art. Intranasal administration can also be by droplet administration to a nasal surface.

Injectable formulations can be prepared in conventional forms, either as liquid solutions or suspensions, solid forms suitable for solution or suspension in liquid prior to injection, or as emulsions. Alternatively, one can administer the pharmaceutical formulations in a local rather than systemic manner, for example, in a depot or sustained-release formulation.

Extemporaneous injection solutions and suspensions can be prepared from sterile powders, granules and tablets of the kind previously described. For example, an injectable, stable, sterile formulation of the invention in a unit dosage form in a sealed container can be provided. The formulation can be provided in the form of a lyophilizate, which can be reconstituted with a suitable pharmaceutically acceptable carrier to form a liquid composition suitable for injection into a subject. The unit dosage form can be from about 1 µg to about 10 grams of the formulation. When the formulation is substantially water-insoluble, a sufficient amount of emulsifying agent, which is pharmaceutically acceptable, can be included in sufficient quantity to emulsify the formulation in an aqueous carrier. One such useful emulsifying agent is phosphatidyl choline.

Pharmaceutical formulations suitable for oral administration can be presented in discrete units, such as capsules, cachets, lozenges, or tables, as a powder or granules; as a solution or a suspension in an aqueous or non-aqueous liquid; or as an oil-in-water or water-in-oil emulsion. Oral delivery can be performed by complexing a compound(s) of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the protein(s) and a suitable carrier (which may contain one or more accessory ingredients as noted above). In general, the pharmaceutical formulations are prepared by uniformly and intimately admixing the compound(s) with a liquid or finely divided solid carrier, or both, and then, if necessary, shaping the resulting mixture. For example, a tablet can be prepared by compressing or molding a powder or granules containing the protein(s), optionally with one or more accessory ingredients. Compressed tablets are prepared by compressing, in a suitable machine, the formulation in a free-flowing form, such as a powder or granules optionally mixed with a binder, lubricant, inert diluent, and/or surface active/dispersing agent(s). Molded tablets are made by molding, in a suitable machine, the powdered protein moistened with an inert liquid binder.

Pharmaceutical formulations suitable for buccal (sub-lingual) administration include lozenges comprising the compound(s) in a flavored base, usually sucrose and acacia or tragacanth; and pastilles comprising the compound(s) in an inert base such as gelatin and glycerin or sucrose and acacia.

Pharmaceutical formulations suitable for parenteral administration can comprise sterile aqueous and non-aqueous injection solutions of the proteins, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical formulations suitable for rectal administration are preferably presented as unit dose suppositories. These can be prepared by admixing the protein(s) with one or more conventional solid carriers, such as for example, cocoa butter and then shaping the resulting mixture.

Pharmaceutical formulations suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical formulation of the present invention with a lipophilic reagent (e.g., DMSO) that is capable of passing into the skin.

Pharmaceutical formulations suitable for transdermal administration can be in the form of discrete patches adapted to remain in intimate contact with the epidermis of the subject for a prolonged period of time. Formulations suitable for transdermal administration can also be delivered by iontophoresis (see, for example, *Pharmaceutical Research* 3:318 (1986)) and typically take the form of an optionally buffered aqueous solution of the compound(s). Suitable formulations can comprise citrate or bis\tris buffer (pH 6) or ethanol/water and can contain from 0.1 to 0.2M active ingredient.

Further, the protein(s) can be formulated as a liposomal formulations. The technology for forming liposomal suspensions is well known in the art. When the compound(s) or salt thereof is an aqueous-soluble salt, using conventional liposome technology, the same can be incorporated into lipid vesicles. In such an instance, due to the water solubility of the protein(s) or salt, the protein(s) or salt will be substantially entrained within the hydrophilic center or core of the liposomes. The lipid layer employed can be of any conventional composition and can either contain cholesterol or can be cholesterol-free. When the protein(s) or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations can be lyophilized to produce a lyophilizate which can be reconstituted with a pharmaceutically acceptable carrier, such as water, to regenerate a liposomal suspension.

Having described the present invention, the same will be explained in greater detail in the following examples, which are included herein for illustration purposes only, and which are not intended to be limiting to the invention.

EXAMPLE 1

Materials and Methods

Strains and Plasmids.

Bacterial strains and plasmids used in this study are described in Table 2. *Escherichia coli* cultures were maintained at 37° C. in Luria-Bertaini (LB; 10 g/L tryptone, 5 g/L yeast extract, 5 g/L NaCl) broth, while *P. aeruginosa* was cultured in LB broth lacking NaCl (LBNS; 10 g/L tryptone, 5 g/L yeast extract). Solid media were prepared by adding 1.0-1.5% select agar (Gibco-BRL). Plasmids in *E. coli* were selected using media supplemented with antibiotics at the following concentrations: carbenicillin (Cb 100 µg ml-1), gentamicin (Gm 10 µg ml$^{-1}$). Plasmids in *P. aeruginosa* were selected on media containing Cb (300 pg ml$^{-1}$), Gm (100 µg ml$^{-1}$), and irgasan (Irg 25 µg ml$^{-1}$). *E. coli* strain JM109 was used for all cloning procedures while *E. coli* SM10 was used to transfer plasmids into P, aeruginosa by bi-parental mating (Toder, (1994) *Methods Enzyymol.* 235:466-474). The *P. aeruginosa* strains used were PAO1 and its derivatives WFPA850, WFPA852, WFPA854, WFPA860, WFPA862, WFPA864, and WFPA866. Vectors pEX18Gm, pEX18Ap or derivatives were used for cloning and gene replacements (Table 2).

Construction of Non-Polar Deletion Mutations in fliC, oprF, and oprI.

To engineer unmarked, non-polar deletion mutations in fliC, oprF, and oprI, we utilized a previously described method (Sundin et al., (2002) *Microbiol. Pathogenesis* 33:265-277). Internal fragments of coding sequences within each gene were deleted using a modified PCR technique termed splicing by overlap extension (Warrens et al., (1977) *Gene* 186:29-35). In this assay, four gene-specific primers were employed in three separate PCR reactions to generate DNA fragments with a defined in-frame deletion of coding sequences within the fliC, oprF, or oprI genes. The primers were also designed such that the final amplicon, harboring the specified deletion allele harbored restriction sites to allow direct cloning into pEX18Ap or pEX18Gm resulting in plasmid pHL150 (ΔfliC), pHL153 (ΔoprF), or pHL155 (ΔoprI). The mutant alleles were introduced into the PAO1 chromosome as outlined (Hoang et al., (1998) *Gene* 212:77-86). The merodiploids were resolved by growing on sucrose-containing media and introduction of the deletion allele, which was verified by PCR.

Recombinant proteins. DNA encoding full-length type A-flagellin of *P. aeruginosa* strain PAK and DNA encoding full-length type B-flagellin of strain PAO1 were each amplified by PCR and ligated into pET29a. DNA encoding the mature OprI antigen of *P. aeruginosa* strain PAO1 (amino acids 21-83) was amplified by PCR and ligated into pET29a or to the 5' end of type A and B-flagellin genes in pET29a generating constructs that encode OprI-type A Flagellin and OprI-type B flagellin. DNA encoding the OprF epitope 8 (amino acids 311-341) of *P. aeruginosa* strain PAO1 was amplified by PCR and ligated into pET29a or to the 5' end of oprI-A-flagellin and oprI-B-flagellin. The structure of each of the final proteins are presented in diagrammatic form in FIG. 1. The nucleic acid and amino acid sequences are shown in Table 1.

All expressed proteins were purified by metal ion affinity chromatography as previously described (Bates et al., (2008) *Mechanisms of Ageing and Development* 129:271-281; Honko et al., (2006) *Infect. Immun.* 74:1113-1120). Acrodisc Q membranes were used to deplete endotoxin and nucleic acids. Endotoxin levels were <10 pg/μg for all of the proteins (as detected by QCL-1000 chromogenic Limulus amebocyte lysate (LAL) test kit, Cambrex Corporation (East Rutherford, N.J.)).

ELISA for TNF-α and Antigen-Specific IgG.

TNF-α levels in cultures of RAW 424 (TLR5$^+$) or RAW 264.7 (TLR5$^-$) cells were measured using a commercial ELISA kit (OptiEIA ELISA, Becton Dickinson) according to the manufacturer's instructions. Data represent three independent experiments with triplicate samples in each experiment.

Titers of antigen-specific IgG were measured using Maxi-Sorb plates coated with 100 μl of antigen (A-flagellin, B-flagellin, OprI, or OprF) at 10 μg/ml in sterile PBS. The plates were incubated overnight at 4° C. and then blocked with 10% newborn calf serum in PBS. Plasma samples (in triplicate) were added, and the plates incubated overnight at 4° C., followed by secondary anti-Ig antibodies (Roche Diagnostics) for 2 h at room temperature. Peroxidase activity was detected with 3,3',5,5'-tetramethylbenzidine (TMB) liquid substrate system (Sigma-Aldrich) and stopped with 2 N $H_2SO_4$. Endpoint dilution titers were defined as the inverse of the lowest dilution that resulted in an absorbance value (at 450 nm) of 0.1 over that of naive plasma. Groups of at least 7 mice were used. To determine relative antibody affinities, the ELISA assay was conducted as described above with the addition of a 15 min incubation with sodium thiocyanate (NaSCN) (Sigma) solution as described previously (Bates et al., (2008) *Mechanisms of Ageing and Development* 129:271-281; Macdonald et al., (1988) *J. Immunol. Methods* 106:191-194).

Mice.

6-8 week old BALB/c and DBA/2 mice were purchased from Charles River Laboratories. All animals were maintained under pathogen-free conditions. All research performed on mice in this study complied with federal and institutional guidelines set forth by the Wake Forest University Animal Care and Use Committee.

Intramuscular (i.m.) Immunization of Mice.

Groups of 7 mice were anesthetized with Avertin (2,2,2-tribromoethanol [Sigma]; tert-amyl alcohol [Fisher]) by intraperitoneal injection. Small volumes (20 μL total) containing antigen and adjuvant in PBS were injected using a 29½ G needle into the right calf of mice. Mice were boosted at 4 weeks via the same route, and bled two weeks later. Plasma was prepared and stored at −70° C. until analysis.

ELISPOT Assay.

The frequency of antigen-specific plasma cells was determined using limiting dilution analysis as previously described (Slifka et al., (1996) *J. Immunological Methods* 199:37-46). Briefly, Immobulin-P high-affinity protein binding ELISPOT plates (Millipore) were coated with 100 μL of A-flagellin, B-flagellin, OprI, or OprF (10 μg/mL) in sterile PBS. Bone marrow and spleen were collected 45 days post boost, single cell suspensions were prepared, and dilutions of the cells ($5\times10^5$/well) were added to the antigen-coated wells. Plates were then incubated at 37° C. for 5 hours, washed, and probed with goat anti-mouse (4° C. overnight). Plates were developed using HRP-Avidin D diluted 1:1000 (Southern Biotechnology) and 3-amino-9-ethylcardbazole (AEC) and dried overnight. Spots were enumerated using a dissecting microscope. Only wells that contained ≥4 spots were counted for analysis. Total spleen cell plasma cell numbers were calculated by multiplying the number of cells in the spleen by the number of spots per million spleen cells. Total bone marrow plasma cell numbers were calculated in the same manner with an additional multiplication by 7.9 to compensate for total bone marrow (Benner et al., (1981) Induction of antibody formation in the bone marrow. In. Immunological Methods II. Levkovitz et al., eds.).

To determine the frequency of antigen-specific memory B cells, the bone marrow and spleen cells were incubated in vitro for 5 days in the presence of 1 μg/mL $OprF_{311-341}$-OprI-Flagellins and then plated as described above. The number of memory B cells was determined by subtracting the number of plasma cells from the 5 hr incubation from the total number of plasma cells after the 5-day culture. Results are shown for two independent experiments.

Antigen-Specific IgG Binding to *P. aeruginosa*.

*P. aeruginosa* strains were incubated with heat-inactivated control or immune mouse plasma for 1 h at 4° C. prior to staining with AlexaFlour647-conjugated anti-mouse IgG (Invitrogen) for 1 hr at 4° C. Data are representative of two experiments with triplicate samples in each experiment.

Antigen-Specific IgG-Mediated Complement Activation.

Control and immune mouse plasma were diluted 1:10 and heat-inactivated at 56° C. for 1 hour prior to use. *P. aeruginosa* strains were grown in LANS broth to an $OD_{600}$ of 0.5 ($\sim10^8$ cfu/mL), washed 2 times with sterile PBS, and then incubated with mouse plasma for 1 hr. The bacteria were then washed and incubated for 1 hr at 37° C. with 5% rabbit serum (Innovative Research) as a source of complement. Finally, the bacteria were stained with goat anti-rabbit C3-FITC (MP Biomedical). Flow cytometric analysis was performed using a BD FACSCaliber and data analyzed with FloJo software (Tree Star, Inc., Ashland, Oreg.). Representative histograms of three experiments are shown. Complement-mediated killing was performed as described above with the exception that the bacteria were incubated for 4 hr with rabbit serum. A time-course experiment revealed minimal killing at 1 hour with rabbit serum (data not shown). Percent bacteria killed was quantitated by (number of input bacteria−number of recovered bacteria)/(number of input bacteria)×100.

Respiratory Challenge with Agar-Embedded *P. aeruginosa*.

*P. aeruginosa* strains were grown in LBNS to $10^8$ cfu/mL. One-part bacteria were added to 9 parts warm (52° C.) 1.5% trypticase soy agar. After five minutes, the agar:bacteria mixture was injected into rapidly spinning warm heavy mineral oil using a 22 gauge needle. The suspension was then mixed for 6 min. The agar beads were then cooled on ice for 20 min and washed 3 times with sterile PBS. The final volume was adjusted to approximately 5 mL. To determine the number of cfu/mL, the agar:bacteria beads were homogenized and bead size determined by comparison to 100-150 μm chromatography beads. Mice (6-7 per group) were anesthetized with Avertin by intraperitoneal injection and then 504 of agar-embedded bacteria were instilled intra-tracheally using a sterile gel-loading tip.

Histology.

Lungs were harvested and transferred to 10% formalin for 24 h. The tissue then was trimmed, embedded in paraffin, cut at 4 μm, and stained with hematoxylin and eosin by routine methods. For histological examination, groups of four mice were used for each condition. Slides were blindly scored on an increasing severity index that incorporates values for consolidation, bronchiolar and vascular degenerative changes, and edema (range for each factor: 0 to 4). Total inflammation score was calculated by the sum of all categories. Representative images (see FIG. 8) are shown from 4 animals/group with 3 sections by animal.

Statistical Analyses.

Statistical analysis was performed using SigmaStat 3.10 (Systat Software, Inc., Point Richmond, Calif.). For normally distributed data sets, significance was determined using the Student's t-test. The significance of data sets, which were not normally distributed, or were of unequal variance were determined using the Mann-Whitney rank sum test. Where applicable a two-way ANOVA test was applied. P values of less than 0.05 were considered significant.

EXAMPLE 2

Results

TLR5-Specific Signaling Activity of *P. aeruginosa* A- and B-Flagellin and $OprF_{311-341}$-OprI-Flagellins.

Figure 2A:
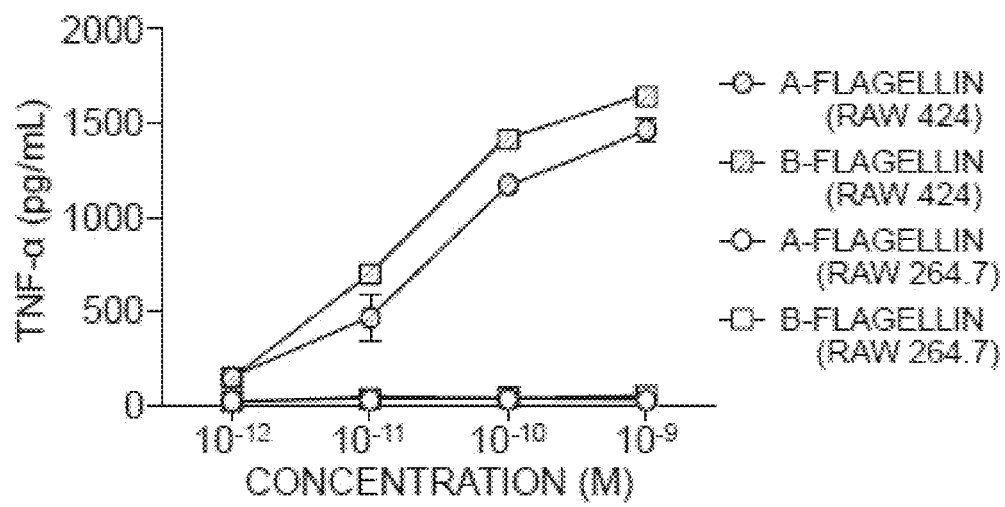
FIGS. 2A-2C. TLR5-specific signaling activity of *P. aeruginosa* A- and B-flagellin and $OprF_{311-341}$-OprI-Flagellins. RAW 424 (TLR5$^+$) and RAW 264.7 (TLR5$^-$) were stimulated with $10^{-9}$ to $10^{-12}$M of protein. At 4 hours post stimulation, supernatants were harvested and the amount of TNF-α was determined by ELISA.
Figure 2B:
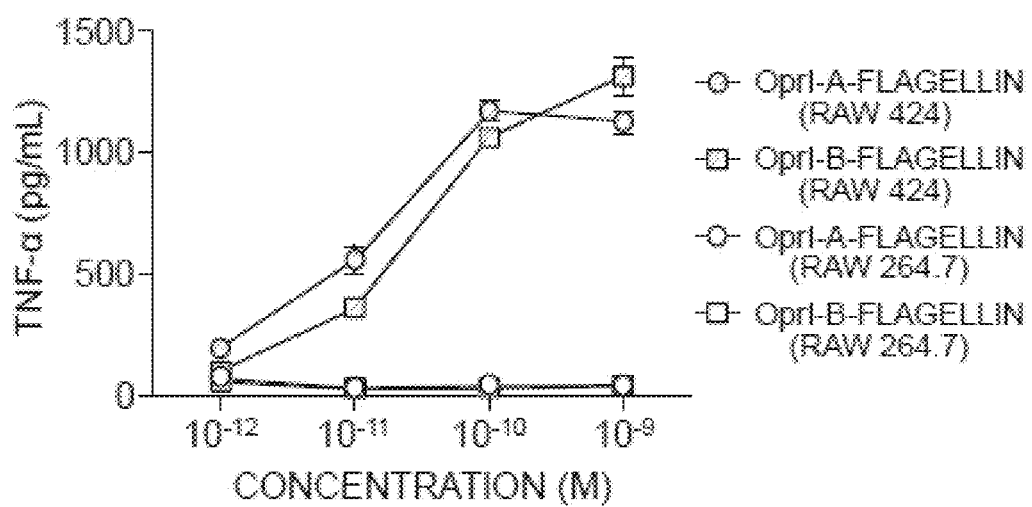
Figure 2C:
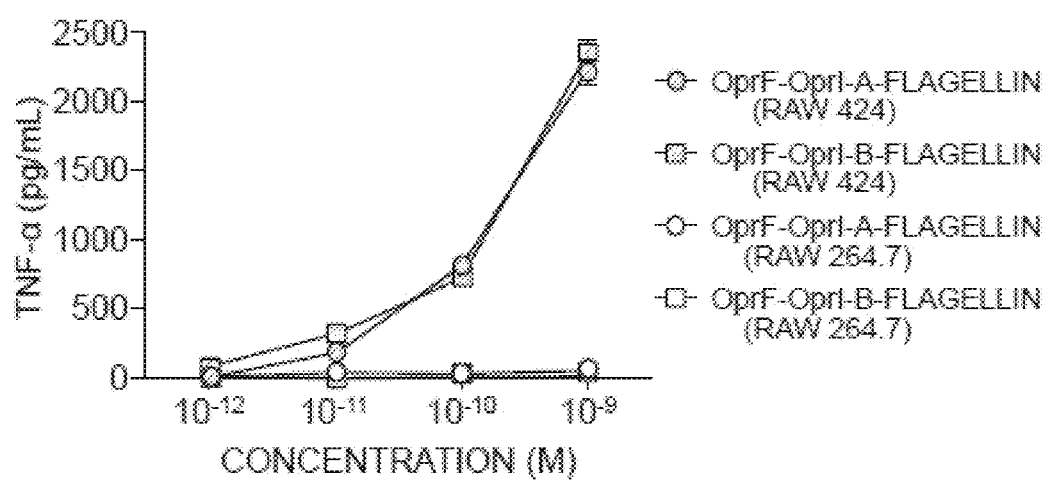

In order to generate antigens with flagellin as the adjuvants, we generated several constructs as shown in FIG. 1. In view of the insertion of the OprF and OprI sequences at the N-terminus of flagellin, it was important to determine if this addition would have a negative impact on the ability of each flagellin, i.e., type A or B, to signal via TLR5. To test the ability of *P. aeruginosa* flagellins either alone or as part of a tri-fusion with OprF and OprI (see FIG. 1), to signal via TLR5, RAW 424 (TLR5$^+$) or RAW 264.7 (TLR5$^-$) cells were incubated with 1 pM-1 nM of each protein and production of TNF-α was assessed. Stimulation of RAW 424 cells with *P. aeruginosa* type A or B-flagellin, OprI-type A or B-flagellin, or $OprF_{311-341}$-OprI-type A or B-flagellin resulted in a concentration-dependent increase in TNF-α (FIGS. 2A-C). In contrast, none of these proteins induced TNF-α production in cultures of TLR5" RAW 264.7 cells. Consistent with previous results with the *P. aeruginosa* flagellins, the half-maximal stimulation occurred at 16 pM for A-flagellin and 40 pM for B-flagellin (Ciacci-Woolwine et al., (1999) *Infect. Immun.* 67:5176-5185. There was no significant difference in the half-maximal stimulation between type A or B flagellin, OprI-type A or B-flagellins, or $OprF_{311-341}$-OprI-type A or B-flagellins. Thus, the presence of OprF-OprI at the N-terminus of type A or B-flagellin does not alter recognition and signaling via TLR5.

Immunization with $OprF_{311-341}$-OprI-Flagellins Promotes a Potent Antigen-Specific Humoral Response.

Figure 3:
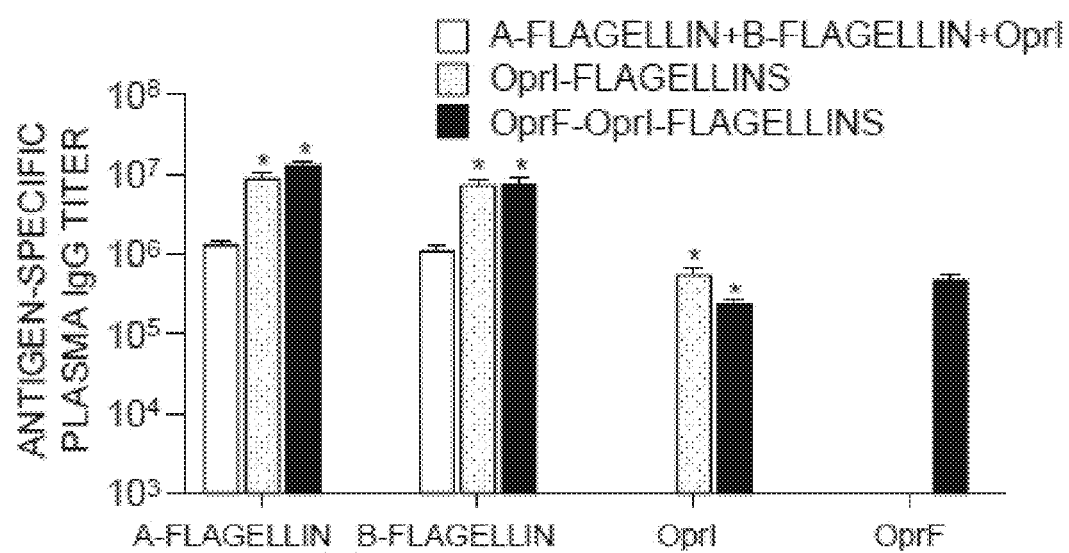
FIG. 3. Immunization with $OprF_{311-341}$-OprI-Flagellins promotes a potent antigen-specific humoral response. BALB/c or DBA/2 mice were immunized intramuscularly with 5 μg of A-flagellin and B-flagellin+10 μg OprI (white bars), 5 μg OprI-A-flagellin+5 μg OprI-B-flagellin (grey bars), or 5 μg $OprF_{311-341}$-OprI-A-flagellin+5 μg $OprF_{311-341}$-OprI-B-flagellin (black bars). At 4 wks post-immunization, animals were boosted and 2 wks post-boost blood was collected and antigen-specific total IgG was determined by ELISA. Data represent at least 7 mice per group in triplicate. *=p<0.05, using a Mann-Whitney rank sum test.

To assess the ability of $OprF_{311-341}$-OprI-A and B-flagellin to promote an antigen-specific humoral response, groups of 7 BALB/c or DBA/2 mice were immunized with 5 μg of each type A and B-flagellin+10 μg OprI, 5 μg OprI-type A and B-flagellin fusion proteins, or 5 μg $OprF_{311-341}$-OprI-type A and B-flagellin fusion proteins. Prior experiments established that immunization of BALB/c mice with 5 μg OprI-Flagellins generated a maximal IgG response to flagellin and OprI (data not shown). Control mice received either OprI or $OprF_{311-341}$-OprI at equivalent molar doses. DBA/2 mice were used because previous studies identified DBA/2 mice as more susceptible to *P. aeruginosa* infection than BALB/c and C57BL/6 mice (Stotland et al., (2000) *Pediatr. Pulmonol.* 30:413-424). Four weeks later, mice were boosted in an identical manner. Two-weeks after the boost the mice were bled and plasma was prepared for analysis of circulating antigen-specific IgG. Mice immunized with OprI-Flagellins or $OprF_{311-341}$-OprI-Flagellins exhibited a robust OprI-specific IgG response (FIG. 3). In contrast, there was no significant OprI-specific IgG in mice given only OprI or type A and B-flagellin+OprI. In all cases, flagellin-specific responses were extremely robust. Mice immunized with $OprF_{311-341}$-OprI-A- and B-flagellin exhibited a high-level of OprF-specific IgG as well as flagellin and OprI-specific IgG.

In addition to determining the titers of antigen-specific IgG following immunization with $OprF_{311-341}$-OprI-A- and B-flagellin, we also evaluated IgG isotypes and IgE. Plasma was prepared from immune mice as described above and antigen-specific IgG subclasses and IgE were determined by ELISA. Immunization of mice with $OprF_{311-341}$-OprI-Flagellins did not elicit any detectable antigen-specific IgE (data not shown). This finding is consistent with our prior work demonstrating that flagellin does not promote antigen-specific IgE responses (Honko et al., (2006) *Infect. Immun.* 74:1113-1120). Although high titers of antigen-specific IgG2a were induced, the overall response to OprI-A- and B-flagellins or $OprF_{311-341}$-OprI-A- and B-flagellin was biased towards IgG1 (data not shown).

Generation of Antigen-Specific Plasma and Memory B Cells (MBC) in Response to $OprF_{311-341}$-OprI-A- and B-Flagellin.

Figure 4A:
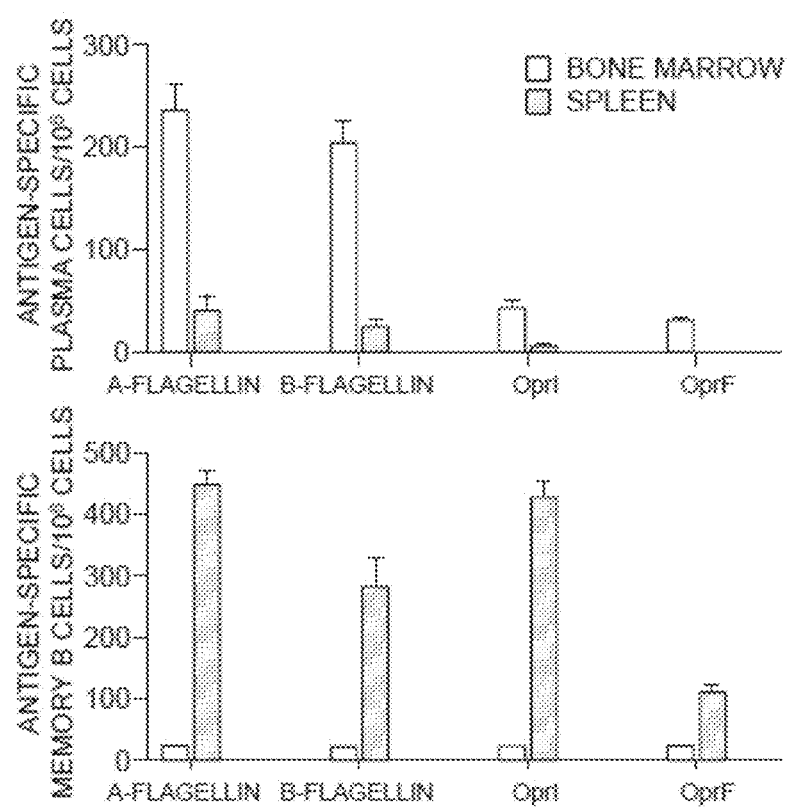
FIGS. 4A-4B. Generation of antigen-specific plasma and memory B cells by $OprF_{311-341}$-OprI-Flagellins immunization. DBA/2 mice were immunized intramuscularly with 5 μg of $OprF_{311-341}$-OprI-Flagellins. Bone marrow and spleens were harvested 40-days post-boost and analyzed for antigen-specific plasma and memory B cells by ELISPOT. Plasma cells were developed following a 5 hr incubation. Memory B cells were stimulated with $OprF_{311-341}$-OprI-Flagellins (1 μg/well) for 5 days and detected following a 5 hr incubation on ELISPOT plates. Results are the average of 2 independent experiments on 5 mice.
Figure 4B:
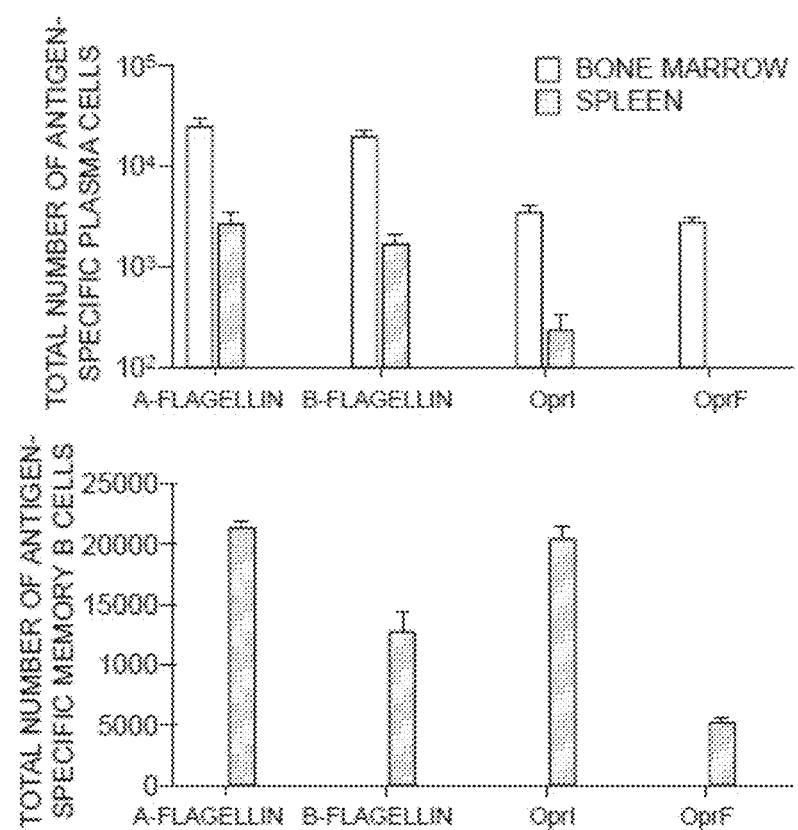

In view of the robust antigen-specific IgG response, we evaluated the frequency of antigen-specific plasma and memory B cells generated in response to $OprF_{311-341}$-OprI-A- and B-flagellin. Mice were immunized with 5 μg of $OprF_{311-341}$-OprI-A- and B-flagellin as described above and 45 days post-boost, bone marrow (BM) and spleen were harvested and the frequency of antigen-specific plasma and memory B cells were determined by ELISPOT. Antigen-specific plasma cells were determined following 5 hr incubation. Eighty-five percent of antigen-specific plasma cells were found in the BM and 15% in the spleen. Consistent with the IgG titer data (FIG. 3), there were more plasma cells for type A- and B-flagellin (~200/10$^6$ BM cells) than OprI (Neville et al., (2005) *Int. J. Mol. Med.* 16:165-171) and OprF (Malhotra et al., (2000) *J. Bacteriol.* 182:6999-7006) (FIG. 4A). No plasma cells were detected in wells that contained cells from non-immune mice. Although significantly more antigen-specific plasma cells were found in the bone marrow, a substantial number of plasma cells remained in the spleen (FIG. 4B). The retention of antigen-specific plasma cells in the spleen correlated with the immunogenicity of each antigen.

In contrast to plasma cells, the generation of MBC was equivalent across flagellins and OprI (FIG. 4A). The fewer number of OprF-specific memory B cells (108 MBC/10$^6$ cells) was not unexpected given the presence of only a single epitope. Nonetheless, our results clearly establish that $OprF_{311-341}$-OprI-A- and B-flagellin elicits not only a significant numbers of plasma cells, but also a substantial pool of memory B cells.

Figure 5:
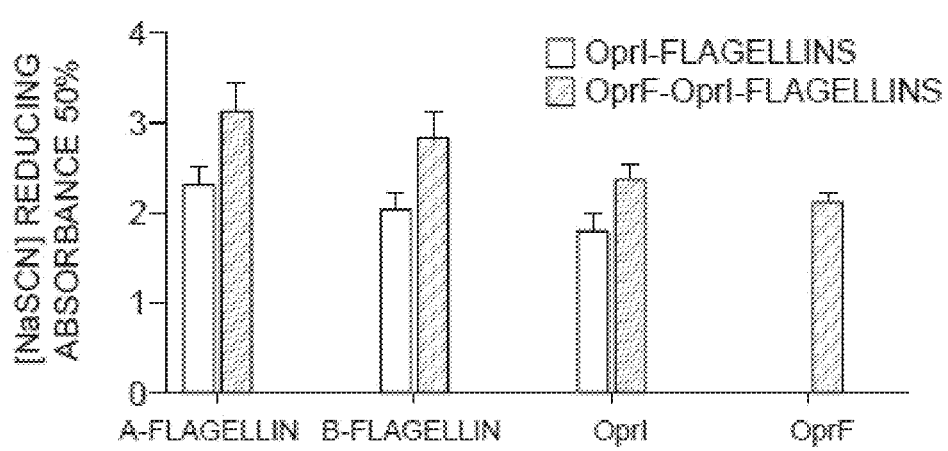
FIG. 5. OprF$_{311-341}$-OprI-Flagellins immunization generates high-affinity antigen-specific IgG. Plasma samples from mice that received OprI-Flagellins or OprF-OprI-Flagellins were used to determine relative antibody affinity for A-flagellin, B-flagellin, OprI, and OprF. Antigen-specific IgG affinity was determined by ELISA using dilutions of sodium thiocyanate (NaSCN). Data are presented as molar concentration of NaSCN required to reduce absorbance 50%. Samples from the same mice were used in the experiments presented in FIGS. 2 and 3. There were 7 mice per group with each sample done in triplicate.

$OprF_{311-341}$-OprI-Flagellin immunization generates high-affinity antigen-specific IgG. Since antigen affinity plays a critical role in the functional activity of an antibody, we evaluated the relative affinity of the IgG generated following immunization with $OprF_{311-341}$-OprI-A- and B-flagellin. The relative affinity of antibodies can be assessed in an ELISA by determining the concentration of sodium thiocyanate required to reduce antibody binding by 50%. As shown in FIG. 5, immunization with OprI-Flagellins or OprF$_{311-341}$-OprI-Flagellins generated IgG with equivalent relative affinities for the three antigens. For comparative purposes, a flagellin+*Y. pestis* F1 antigen vaccine generated F1-specific IgG requiring 3M sodium thiocyanate for 50% reduction in binding (Bates et al., (2008) *Mechanisms of Ageing and Development* 129:271-281). Given the observation that these antibodies provide complete protection against respiratory challenge with *Y. pestis* (Honko et al., (2004) *Infect. Immun.* 74:1113-1120; Mizel et al., (2009) *Clinical and Vaccine Immunology* 16:21-28), we have defined high affinity IgG as those antibodies requiring 2-3 M sodium thiocyanate for 50% reduction in antigen binding. OprF$_{311-341}$-OprI-A- and B-flagellin immune plasma had an average relative IgG affinity approaching 3 M for flagellin, OprI, and OprF (FIG. 5). Thus, the data are consistent with the conclusion that OprF$_{311-341}$-OprI-A- and B-flagellin elicits high-affinity antigen-specific IgG.

Complement Activating Activity of Antibodies Specific for OprI, OprF, and Type A and B-Flagellins.

Figure 6A:
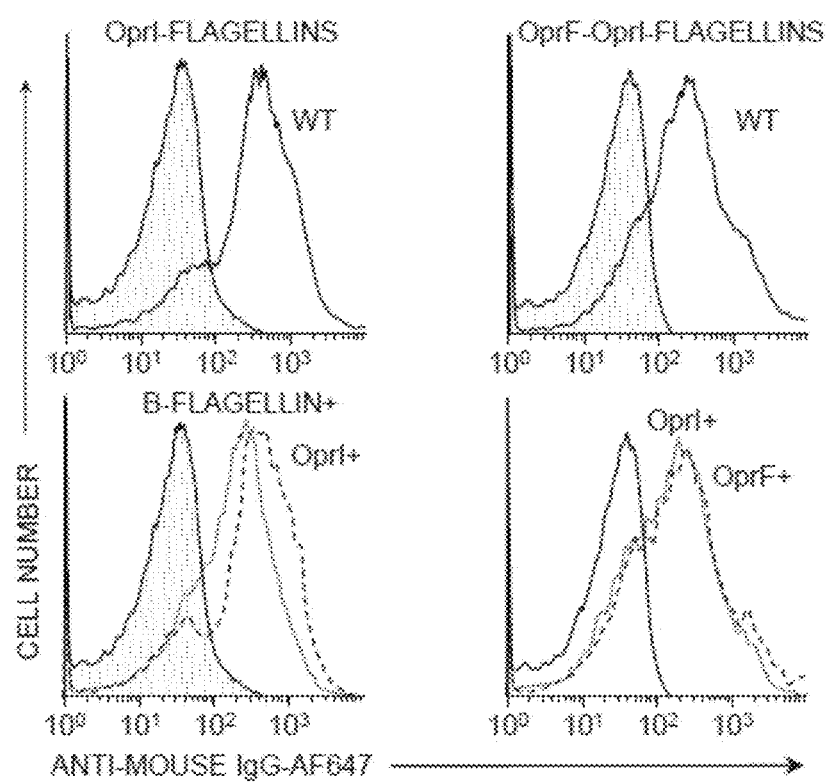
FIGS. 6A-6C. Complement activating activity of OprI, OprF, and type A and B-flagellin-specific IgG. Plasma samples from OprF$_{311-341}$-OprI-Flagellins were incubated with *P. aeruginosa* and IgG binding and C3 deposition was determined by flow cytometry. The antigens expressed by each *P. aeruginosa* strain are shown.

To assess the functional activity of each of the antigen-specific IgG, it was first necessary to generate *P. aeruginosa* mutants lacking one or more of these antigens (see Table 2 and Example 1). *P. aeruginosa* type-B-flagellin expressing strain PAO1 was used as the genetic background for the mutants. Each mutant exhibited growth kinetics that were similar to that of the wild-type strain (data not shown). *P. aeruginosa* strains were incubated with immune or control mouse plasma at 4° C. for 1 hour and then stained for the presence of IgG. As shown in FIG. 6A, wild-type *P. aeruginosa* bound significant amounts of IgG specific for flagellin, OprI, and OprF. Furthermore, mutants positive for only flagellin, OprF, or OprI also bound high levels of IgG. Experiments using a type-A-flagellin expressing strain, PAK, demonstrated similar results (data not shown). These results demonstrate that the antibodies generated against the recombinant fusion protein recognize these antigens in their cell-associated forms. This is particularly important in the case of OprF, since only a single epitope was present in the OprF$_{311-341}$-OprI-flagellin fusion proteins.

Figure 6B:
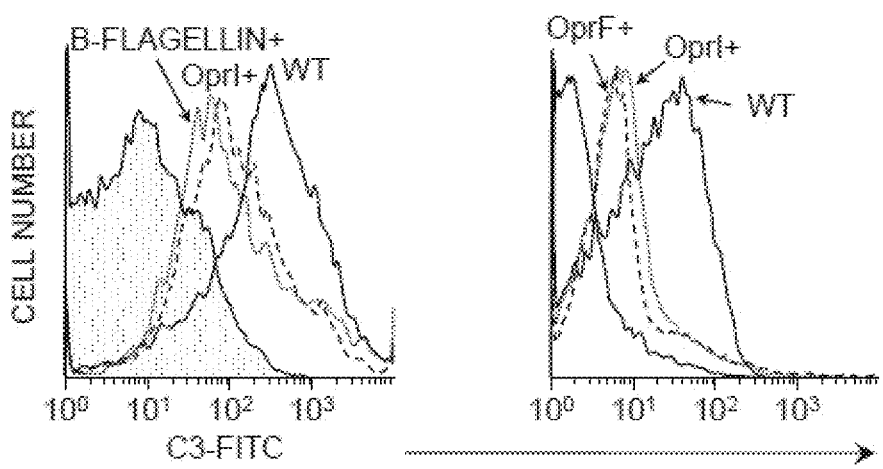
Figure 6C:
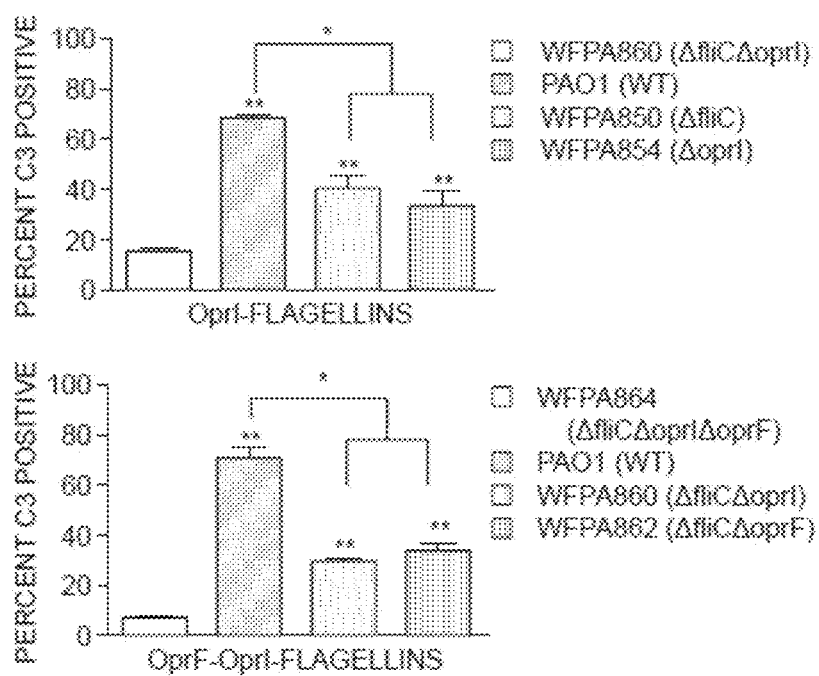

Having established the ability of the individual populations of IgG to recognize the cell-associated antigens, we next evaluated the potential of these antibodies to activate complement. Previous work has clearly established the importance of the complement system in the clearance of *P. aeruginosa* (Eckhardt et al., (1991) *Zentralbl. Bakteriol.* 275:100-111; Mueller-Ortiz et al., (2004) *Infect. Immun.* 72:2899-2906; Schiller (1988) *Infect. Immun.* 56:632-639; Younger et al., (2003) *Am. J. Respiratory Cell Molecular biology* 29:432-438). To assess the ability of antibodies specific for OprF, OprI, type A and B-flagellin IgG to activate complement, we measured the extent of IgG-dependent C3 deposition on *P. aeruginosa*. The various *P. aeruginosa* strains were incubated with a 1:10 dilution of heat-inactivated immune mouse plasma for 1 hour, and then 5% rabbit complement was added for an additional hour. The bacteria were then stained with FITC-labelled C3-specific antibody and the extent of C3-deposition was determined by flow cytometry. A time course revealed that 1-hour incubation with serum was optimal for C3 deposition and yielded minimal cell death (data not shown). As a control, we used a *P. aeruginosa* strain lacking flagellin, OprI, and OprF. OprI-A- and B-flagellin or OprF$_{311-341}$-OprI-A- and B-flagellin immune plasma promoted significant C3 deposition on the surface of wild-type *P. aeruginosa* (FIG. 6A). By using mutants that lack one or more of the eliciting antigens, we found that IgG with specificity for each of the eliciting antigens promoted robust C3 deposition (FIGS. 6B-C) When all three antigens were present, there was a synergistic increase in the level of C3 deposition. These results indicate that OprF$_{311-341}$-OprI-A- and B-flagellin immunization generated antigen-specific IgG that exhibited a high-degree of functional activity and that the combination of flagellins, OprI, and OprF-specific IgG triggered the highest level of C3 deposition.

Antibody-Dependent, Complement-Mediated Killing of *P. aeruginosa* by OprF$_{311-341}$-OprI-A- and B-Flagellin Immune Plasma.

Figure 7:
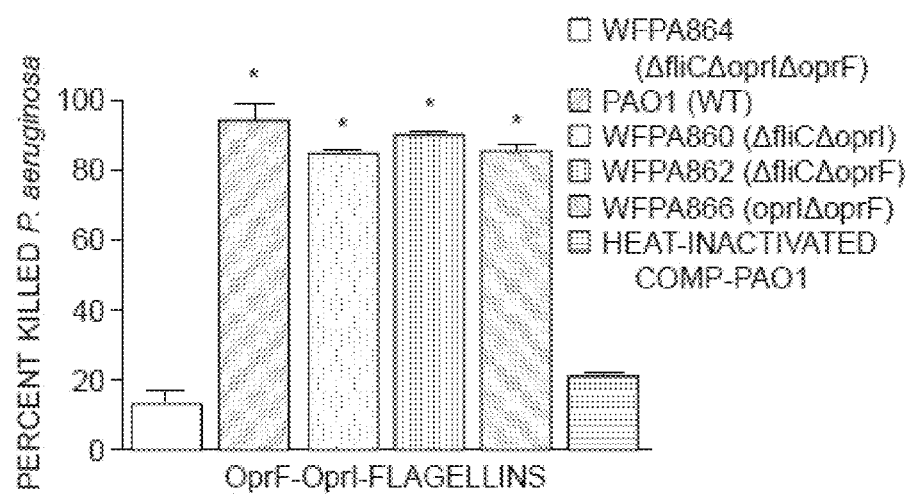
FIG. 7. Antibody-dependent complement-mediated killing of *P. aeruginosa* by OprF$_{311-341}$-OprI-Flagellins immunized mouse plasma. Plasma samples from OprF$_{311-341}$-OprI-Flagellins immunized mice were diluted 1:10 and heat-inactivated at 56° C. for 1 hr. Samples were then supplemented with 5% rabbit complement for 4 hr at 37° C. Data are from 4 samples over two experiments, each sample done in duplicate. *p<0.05, using Student's t-test.

In view of the robust ability of OprF, OprI, and type A and B-flagellin-specific IgG to promote C3 deposition, we next examined the ability of those antibodies to promote complement-mediated killing of *P. aeruginosa*. Bacteria were incubated with heat-inactivated immune plasma for 1 hr and then 5% rabbit complement was added for an additional 4 hr at 37° C. It is important to note that like wild-type bacteria, the *P. aeruginosa* mutants were not susceptible to significant nonspecific killing by normal serum (data not shown). Approximately 90% of wild-type, nonmucoid *P. aeruginosa* (PAO1, PAK, and 1286) as well as strains expressing B-flagellin, OprI, or OprF were susceptible to antibody-dependent complement mediated killing (FIG. 7 and Table 3). In contrast, only 18% of mucoid *P. aeruginosa* (T68933 and PD0300M) were susceptible to killing (Table 3). This result is not unexpected, given the presence of a large amount of alginate exopolysaccharide in the mucoid strains that would likely mask OprI and OprF. In support of this conclusion, we found that a strain of PAO1 (PD0300NM) deficient in alginate production (and thus nonmucoid) was quite sensitive to killing (Table 3). In addition, the generally applicable inverse relationship between flagella and alginate expression (Tart et al., (2005) *J. Bacteriol.* 187:7955-7962) would also limit the effectiveness of the flagellin-specific IgG. The antigen-dependence of the killing was evidenced by the very low level of killing with bacteria lacking all three of the eliciting antigens. When the source of complement was heat-inactivated, only background levels of killing were observed. Taken together, these findings clearly demonstrate that the antibodies generated in response to OprF$_{311-341}$-OprI-A- and B-flagellin exhibit potent antigen binding, complement activating activity, and killing of nonmucoid, but only modest activity against mucoid *P. aeruginosa*.

Enhanced Clearance of *P. aeruginosa* in OprF$_{311-341}$-OprI-Flagellins Immunized Mice.

Figure 8:
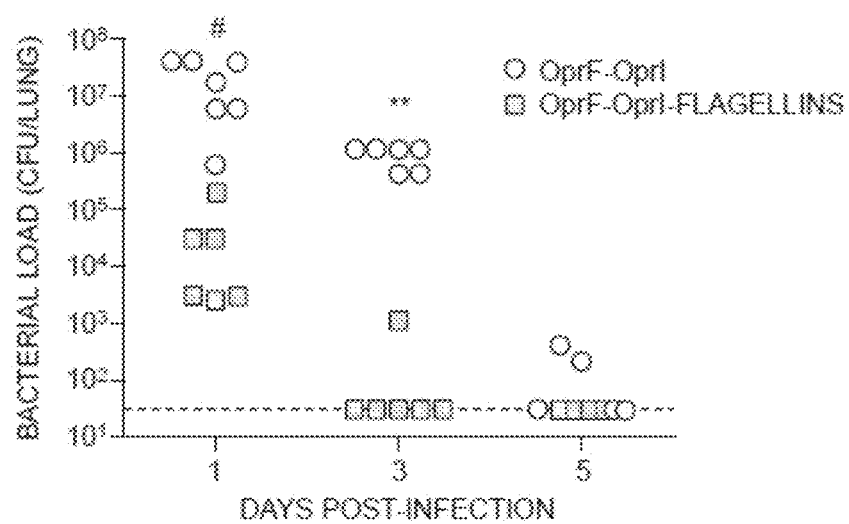
FIG. 8. OprF$_{311-341}$-OprI-Flagellins immunized mice display enhanced rate of clearance following pulmonary *P. aeruginosa* challenge. DBA/2 mice were immunized twice with 5 μg of OprF$_{311-341}$-OprI-Flagellins and challenged intratracheally with 3.5×10$^6$ cfu of agar-embedded PAO1. The right lungs were harvested 1, 3, and 5 days post-infection and bacterial burden was assessed by counting. Data are the average of 6-7 mice per group. Dotted line indicates the limit of detection. #p=0.053, **p=0.002, using a Mann-Whitney rank sum test.

Nonmucoid *P. aeruginosa* does not cause a chronic infection in healthy mice as it does in CF patients. If large doses of bacteria are used, the mice quickly succumb to bacteremia (Weimer, Wozniak, and Mizel, unpublished observations). With small doses, the mice rapidly clear the bacteria. In view of the lack of a suitable animal model that closely mimics the situation in CF patients, i.e., chronic infection, investigators have evaluated agar-embedded mucoid *P. aeruginosa* as a way to infect mice such that rapid septic shock is avoided and the time of infection is lengthened (Kikuchi et al., (2001) *J. Clin. Invest.* 108:917-927; Tam et al., (1999) *Am. J. Respiratory Cell Molecular Biology* 20:710-719). For example, Stevenson and colleagues (Stotland et al., (2000) *Pediatr. Pulmonol.* 30:413-424; Tam et al., (1999) *Am. J. Respiratory Cell Molecular Biology* 20:710-719) used the agar bead model to demonstrate that DBA/2 mice were more susceptible to mucoid *P. aeruginosa* than were BALB/c or C57BL/6 mice. However, since the initial *P. aeruginosa* infection in CF patients is mediated by nonmucoid strains (Burns et al., (2001) *J. Infect. Diseases* 183:444-452; Li et al., (2005) *JAMA* 293:581-588; Tosi et al., (1995) *J. Infect. Diseases* 172:453-461), we felt it was more appropriate to use nonmucoid bacteria in the agar bead model. Preliminary results revealed that unimmunized mice did not succumb when infected intra-tracheally with up to $3.5 \times 10^6$ cfu of nonmucoid P. aeruginosa embedded in agar beads, but the mice did exhibit substantial morbidity. In view of the finding that DBA/2 mice are more susceptible to P. aeruginosa, we used this strain to evaluate the ability of $OprF_{311-341}$-OprI-Flagellins immunization to promote enhanced clearance of P. aeruginosa embedded in agar. DBA/2 mice were immunized as described in Example 1 and infected intratracheally with $3.5 \times 10^6$ cfu agar-embedded PAO1. Lungs were harvested 1, 3, and 5 days post-infection and bacteria enumerated by serial dilutions on LANS plates. One day after challenge, immunized mice displayed a marked decrease in bacterial burden compared to control mice (FIG. 8). After 3 days, 5 of 6 mice immunized with $OprF_{311-341}$-OprI-Flagellins had cleared the infection. In contrast, the control mice had large numbers of bacteria in the lungs. Although the control mice cleared the infection by day 5, our results clearly demonstrate that immunization with $OprF_{311-341}$-OprI-Flagellins had a dramatic effect on the rate of bacterial clearance. It is important to emphasize that the ability of mice immunized with OprF-OprI to clear the infection by day 5 reflects a limitation of this model and not the efficacy of the $OprF_{311-341}$-OprI-Flagellins vaccine.

Figure 9A:
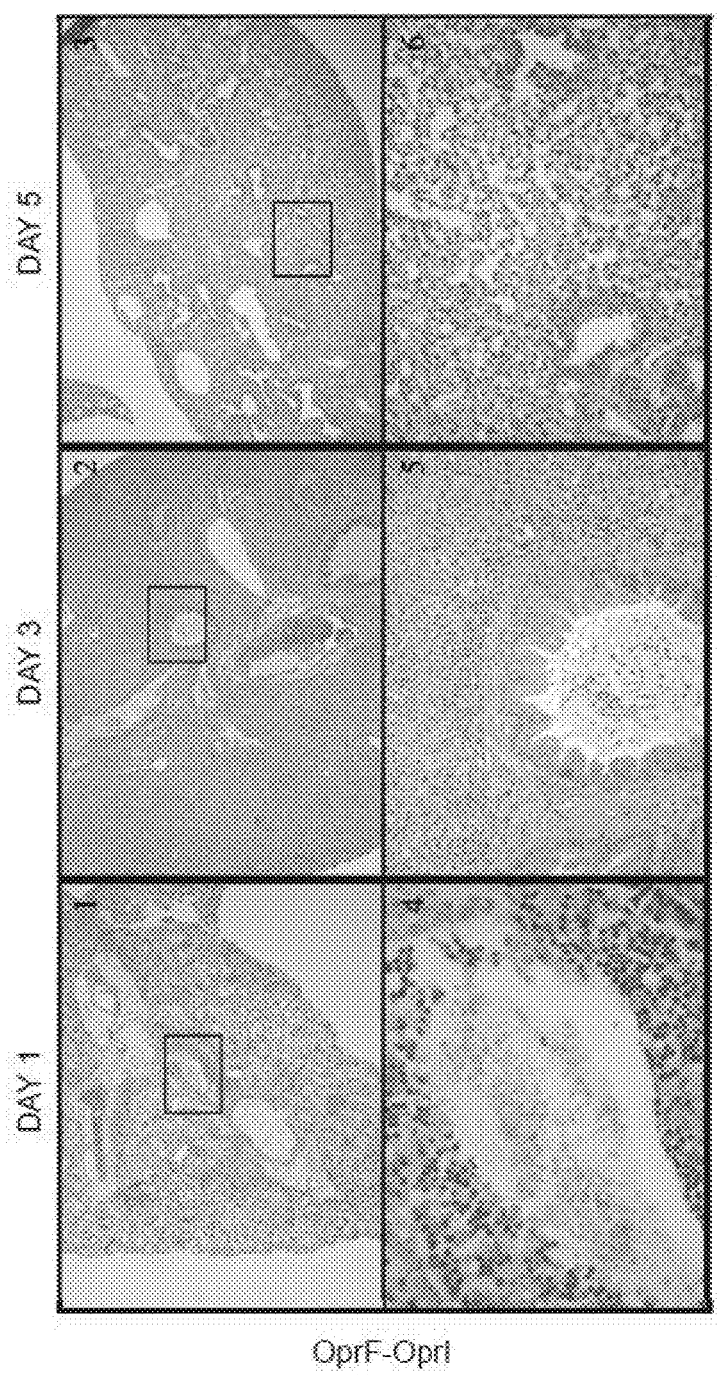
FIGS. 9A-9C. OprF$_{311-341}$-OprI-Flagellins immunized mice are protected against severe lung pathology during pulmonary *P. aeruginosa* challenge. The left lung of identical mice used in FIG. 7 was evaluated for histology. Lungs were fixed in 10% formalin for 24 hours, paraffin embedded, and 4 μm sections were cut. Slides were stained with H&E. Representative images are shown from 6 sections/animal.
Figure 9B:
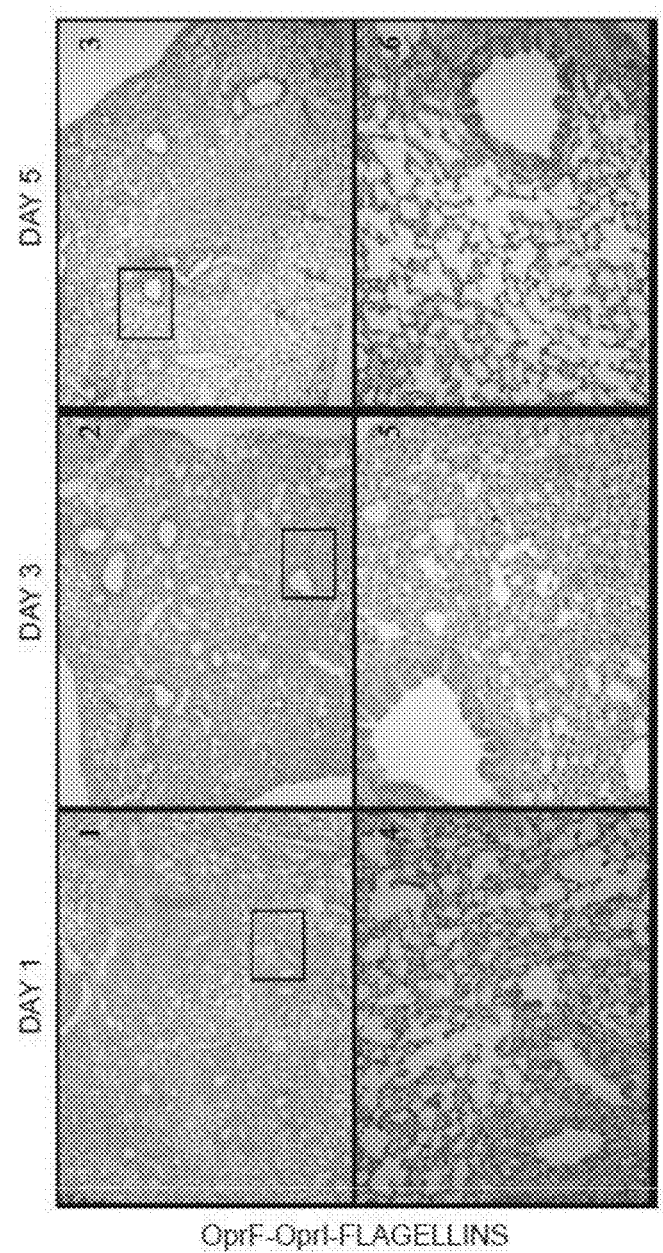
Figure 9C:
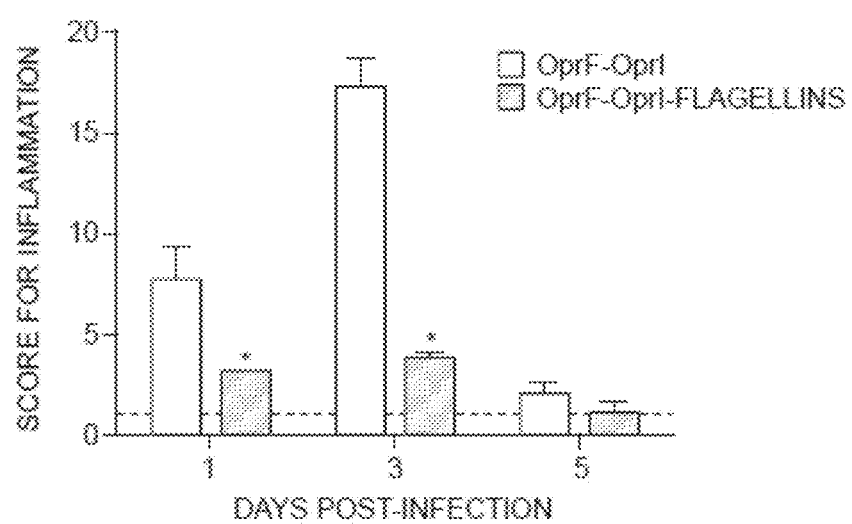

Reduced lung pathology following pulmonary P. aeruginosa challenge in $OprF_{311-341}$-OprI-Flagellin immunized mice. In addition to determining bacterial burden following challenge, we also evaluated the histopathology of lungs from mice immunized with $OprF_{311-341}$-OprI-Flagellin or OprF-OprI. Lungs were harvested 1, 3, and 5 days after P. aeruginosa challenge. One day after P. aeruginosa challenge, alveolar walls from $OprF_{311-341}$-OprI-Flagellin immunized mice displayed slight thickening owing to congestion and increased numbers of inflammatory cells. In contrast, lungs from mice immunized with OprF-OprI developed bronchopneumonia, with airway-oriented neutrophils, edema, and abundant visible bacteria (FIG. 9A). After 3 days, immune mice exhibited only minor inflammatory changes in the lung, whereas more severe pneumonia with diffuse consolidation was present in the control animals. After 5 days, the lungs of immune mice were normal, while those of the controls had thickened alveolar walls, a result of congestion and inflammatory cells (FIG. 9B). In summary, mice immunized with $OprF_{311-341}$-OprI-Flagellin displayed minimal lung pathology which completely resolved by day 5 post challenge. The absence of lung pathology in the immune mice not only demonstrates the efficacy of the vaccine in promoting bacterial clearance, but also the ability of the vaccine to promote clearance without inducing secondary tissue damage. In striking contrast, mice immunized with OprF-OprI demonstrated severe pneumonia which only partially resolved by day 5 (FIG. 9A). In conjunction with the results of in vitro experiments (FIGS. 5 and 6), it is clear that $OprF_{311-341}$-OprI-Flagellin immunization promotes an adaptive immune response that promotes the generation of antigen-specific IgG that exhibits robust functional activity, facilitates rapid clearance, and prevents the development of severe pneumonia following P. aeruginosa infection.

The goal of the studies described above were two-fold: to establish a set of criteria for a vaccine against P. aeruginosa and then to develop and test the vaccine based on these criteria. Based on our results, we conclude that the $OprF_{311-341}$-OprI-A- and B-flagellins vaccine meets all of the proposed criteria: the vaccine contains flagellin, a potent adjuvant, is multivalent, generates high-titer antigen-specific IgG that exhibits a high degree of functional activity, generates a robust memory response, and enhances clearance of nonmucoid P. aeruginosa without secondary tissue damage. Although the antigen-specific IgG induced by this vaccine did not promote a robust complement-mediated killing of mucoid P. aeruginosa, it is important to emphasize that longitudinal studies of CF patients have clearly demonstrated that the initial P. aeruginosa infection is mediated by nonmucoid bacteria (Burns et al., (2001) *J. Infect. Diseases* 183:444-452; Li et al., (2005) *JAMA* 293:581-588; Toder et al., (1994) *Methods Enzymol.* 235:466-474). We have shown that multivalency not only promotes synergistic activity of individual antibodies in activating complement but also enhances vaccine coverage against nonmucoid P. aeruginosa strains (FIG. 6).

The titers of flagellins, OprI, and OprF-specific IgG following immunization with $OprF_{311-341}$-OprI-Flagellins are in most cases two logs higher than those reported in other studies (Doring et al., (2007) *Proc. Nat. Acad. Sci.* 104: 11020-11025; Holder et al., (1986) *J. Trauma* 26:118-122; Sadikot et al., (2005) *Am. J. Respiratory and Critical Care Medicine* 171:1209-12223; Saha et al., (2007) *J. Immunol.* 179:1147-1154; Wat et al., (2008) *J. Cyst. Fibros.* 7: 85-88; Worgall et al., (2007) *J. Virol.* 81:13801-13808; Younger et al., (2003) *Amer. J. Respiratory Cell and Molecular Biology* 29:432-438). For example, von Specht et. al. (Tosi et al., (1995) *J. Infect. Diseases* 172:453-461) required three immunizations with 70-fold more antigen to achieve equivalent antibody responses. The difference may be due to the extraordinary potency of flagellin as an adjuvant, as well as the use of fusion proteins that enhance the efficiency of antigen delivery to dendritic cells via the binding of the associated flagellin to TLR5 on these cells (Bates et. al., submitted for publication). The finding that immunization with $OprF_{311-341}$-OprI-Flagellins promotes the generation of large numbers of plasma cells is consistent with the very high titers of induced IgG. Furthermore, the generation of immunologic memory is evidenced by the relatively high frequency of antigen-specific MBC.

The major cause of chronic inflammation in CF patients is persistent P. aeruginosa infection. Over-production of alginate and subsequently, biofilm development allows P. aeruginosa to evade the immune system and also increases antibiotic resistance, making it extremely difficult to eradicate the infection (Burns et al., (2001) *J. Infectious Diseases* 183:444-452; Li et al., (2005) *JAMA* 293:581-588). Mucoid conversion is also associated with a significant decrease in lung function in CF patients (Mueller-Ortiz et al., (2004) *Infect. Immun.* 72:2899-2906). Our findings indicate the optimal time to vaccinate CF patients using $OprF_{311-341}$-OprI-A- and B-flagellin would be prior to mucoid conversion, since only modest levels of complement-mediated killing occurred in mucoid bacteria (FIG. 7 and Table 3).

The foregoing is illustrative of the present invention, and is not to be taken as limiting thereof. The invention is defined by the following claims, with equivalents of the claims to be included therein.

TABLE 1

Nucleic Acid and Amino Acid Sequences of Fusion Proteins.

OprF-Opr I-A-Flagellin (the italicized positions are the cut sites used for cloning)

Nucleic acid sequence (SEQ ID NO: 5):
ATGGAAGGTGGTCGCGTGAACGCTGTTGGTTACGGCGAGTCCCGCCCGGTTGCCGACAACGCCACCGCTGAAGGC
CGCGCTATCAACCGTCGCGTTGGCGGTGGCGGT*GGATCC*ACGAGCCACTCCAAAGAAACCGAAGCTCGTCTGACC
GCTACCGAAGACGCAGCTGCTCGTGCTCAGGCTCGCGCTGACGAAGCCTATCGCAAGGCTGACGAACCTCTCCGC
GCTGCTCAGAAAGCTCAGCAGACTGCTGACGAGCCTAACGAGCGTGCCCTGCCCATGCTGGAAAAAGCCAGCCGC
AAG *AAGCTT*gccttgaccg

```
     421 tcaacaccaa catcgcttcg ctgaacactc agcggaacct gaacaactct tccgcgtcgc
     481 tgaacacttc gctgcagcgt ctgtccaccg ttcgcgcat caacagcgca aaggacgacg
     541 ccgccggcct gcagatcgcc aaccgtctga ccagccaggt caacggcctg aacgtggcta
     601 ccaagaacgc caacgacggt atctccctgg cgcagaccgc tgaaggcgcc ctgcagcagt
     661 cgaccaacat cctgcagcgt atgcgtgacc tgtccctgca gtcggccaac ggctccaaca
     721 gcgactccga gcgtaccgct ctgaacggca agcgaagcg actgcagaaa gaactggatc
     781 gtatcagcaa caccaccacc ttcggtggcc gcaagctgct cgacggttgc ttcggcgtcg
     841 ccagcttcca ggtgggttcg gccgccaacg aaatcatcag cgtcggcatc gacgagatga
     901 gcgcagagtc gctgaaccgc acctacttca aggctgacgg cggcggcgcg gtcactgctg
     961 caaccgcttc gggcaccgtc gacatcgcga tcggcatcac cggcggcagc gccgtgaacg
    1021 tcaaggtcga catgaagggc aacgaaaccg ccgagcaggc ggctgccaag atcgccgcag
    1081 cggtcaacga cgccaacgtc ggcatcggtg ccttcagcga cggcgatacc atcagctatg
    1141 tttccaaagc tggcaaggat ggctccggtg cgatcactag cgcggtttcc ggcgttgtca
    1201 tcgctgacac cggcagcgacc ggcgtaggca ccgcggctgg cgtagcccct tccgctaccg
    1261 cttcgccaa gaccaacgac accgtcgcca agatcgacat ctccaccgcg aaggcgctca
    1321 gtcgccgtgc tggtgatcgc acgacggcga tcaagcagat cgacgccagc gtgccgacct
    1381 cggtcgcggt gcagaaccgc ttcgacaaca ccatcaacaa cctgaagaac atcggtgaga
    1441 acgtatcggc tgctcgcggc cggatcgaag acaccgactt cgcagccgaa accgccaacc
    1501 tgaccaagaa ccaagtgctg caacaagccg gcaccgcgat cctggcccag gccaaccagc
    1651 tgccgcagtc ggttctgagc ctgctgcga
```

Amino acid sequence (SEQ ID NO: 6):

Underlined amino acids are the conserved regions, bold amino acids are the hyper-variable
region

```
MetEGGRVNA VGYGESRPVA DNATAEGRAI NRRVGGGGGS SSHSKETEAR LTATEDAAAR  60
AQARADEAYR KADEALGAAQ KAGGTADEAN ERALPMetLE KASRKKLALT VNTNIASLNT 120
QRNLNNSSAS LNTSLQRLST GSRINSAKDD AAGLQIANRL TSQVNGLNVA TKNANDGISL 180
AQTAEGALQQ STNILQRMet RDLSLQSANG SNSDSERTAL NGEAKQLQKE LDRISNTTTF 240
GGRKLLDGSF GVASFQVGSA ANEIISVGID EMetSAESLN GTYFKADGGG AVTAATASGT 300
VDIAIGITGG SAVNVKVDMe tKGNETAEQA AAKIAAAVND ANVGIGAFSD GDTISYVSKA 360
GKDGSGAITS AVSGVVIADT GSTGVGTAAG VAPSATAFAK TNDTVAKIDI STAKALSRRA 420
GDRTTAIKQI DASVPTSVAV QNRFDNTINN LKNIGENVSA ARGRIEDTDF AAETANLTKN 480
QVLQQAGTAI LAQNQLPQS VLSLLR
```

OprF-Opr I-B-Flagellin (the italicized positions are the cut sites used for cloning)

Nucleic Acid Sequence (SEQ ID NO: 7):
ATGGAAGGTGGTCGCGTGAACGCTGTTGGTTACGGCGAGTCCCGCCCGGTTGCCGACAACGCCACCGCTGAAGGC
CGCGCTATCAACCGTCGCGTTGGCGGTGGCGGT*GGATCC*AGCAGCCACTCCAAAGAAACCGAACCTCGTCTGACC
GCTACCGAAGACGCCAGCTGCTCGTGCTCAGGCTCGCGCTGACGAAGCCTATCGCAAGGCTGACGAAGCTCTGGGC
GCTGCTCAGAAAGCTCAGCAGACTGCTGACGAGCCTAACGAGCGTGCCCTGCCGCATGCTGGAAAAAGCCAGCCGC
AAG*AAGCTT*GCCCTTACAGTCAACACGAACATTGCTTCCCTGAACACTCAGCGCAACCTGAATGCTTCTTCCAAC
GACCTCAACACCTCGTTGCAGCGTCTGACCACCGGCTACCCCATCAACAGTGCCAAGGACGATGCTGCCGGCCTG
CAGATCTCCAACCGCCTGTCCAACCAGATCAGCGGTCTGAACGTTGCCACCCGCAACGCCAACGACGGCATCTCC
CTGGCGCAGACCGCTGAAGGTGCCCTGCAGCAGTCCACCAATATCCTGCAGCGTATCGCGGACCTGGCCCTCCAA
TCCGCCAACGGCTCCAACAGCGACGCCGACCGTGCCGCCCTGCAGAAAGAAGTCGCTGCGCAACAGGCCGAACTG
ACCCGTATCTCCGATACCACCACCTTCGGTGGCCGCAAGCTGCTCGACGGCTCCTTCGGCACCACCAGCTTGCAG
GTCGGTTCCAACGCCTACGAGACCATTGACATCAGCCTGCAGAATGCCTCTGCCAGCGCCATCGGTTCTTACCAG
GTCGGCAGCAACGGCGCGGGTACCGTCGCCAGCGTAGCGGGCACCGCGACCGCTTCGGGCATCCCCTCCGGCACC
GTCAACCTGGTCGGTGGCGGTCAGGTGAAGAACATCGCCATCGCCGCCGGCGATAGCGCCAAGGCCATCGCCGAG
AAGATGGACGGTGCGATCCCGAACCTGTCGGCTCGTGCCCGTACCGTGTTCACCGCTGATGTCAGCGGCGTGACC
GGTGGTTCGCTGAACTTCGACGTAACCGTTGGCAGCAACACCGTGAGCCTGGCAGGCGTGACCTCCACTCAGGAT
CTGGCCGACCAACTGAACTCCAACTCGTCGAAGCTGCGCATCACTGCCAGCATCAACGACAAGGGTGTACTGACC
ATCACCTCCGCTACCGGCGAGAACGTCAACTTCGGTGCGCAGACCGGTACCGCTACTGCCGGTCAGGTCGCAGTG
AAGGTCCAGGGTTCCGACGGCAAGTTCGAAGCGGCCGCCAAGAACGGTGGTAGCTGCCGGCTACTGCCGCTACCGGC
ACCATCGTGACCGGCTACGTGCAACTGAACTCGCCGACCGCCTACTCGGTCAGCGGTACCGGCACCCAGGCTTCG
CAGGTCTTCGGCAACGCCAGCGCCGCGCAGAACAGCAGCGTTGCCAGCGTCGACATCTCCACTGCCGACGGCGCC
CAGAACGCCATCGCGGTAGTCGATAACGCCCTGGCTGCGATCGACGCCCAGCGTGCTGACCTCGGTGCTGTTCAG
AACCGCTTCAAGAACACTATCGACAACCTGACCAACATCTCGGAAAACGCTACCAACGCTCGTAGCCGCATCAAG
GACACCGACTTCGCTGCCGAAACCGCGGCGCTGTCGAAGAACCAGGTGCTGCAACAGGCCGGTACCGCGATCCTG
CCCAGGCCAACCAGCTGCCGCAGGCGGTCCTGAGCCTGCTCCGC TABLE 1-continued Nucleic Acid and Amino Acid Sequences of Fusion Proteins.

Amino acid sequence (SEQ ID NO: 8):

Underlined amino acids are conserved regions and bold amino acids are part of the hypervariable region

```
MetEGGRVNA VGYGESRPVA DNATAEGRAI NRRVGGGGGS SSHSKETEAR LTATEDAAAR  60
AQARADEATR KADEALGAAQ KAGGTADEAN ERALAMetLR KASRKKLALT VNTNIASLNT 120
QRNLNASSND LNTSLQRLTT GYRINSAKDD AAGLQISNRL SNQISGLNVA TRNANDGISL 180
AQTAEGALQQ STNILQRIRD LALQSANGSN SDADRAALQK EVAAQQAELT RISDTTTFGG 240
RKLLDGSFGT TSFQVGSNAY ETIDISLQNA SASAIGSYQV GSNGAGTVAS VAGTATASGI 300
ASGTVNLVGG GQVKNIAIAA GDSAKAIAEK MetDGAIPNL SARARTVFTA DVSGVTGGSL 360
NFDVTVGSNT VSLAGVTSTQ DLADQLNSNS SKLGITASIN DKGVLTITSA TGENVKFGAQ 420
TGTATAGQVA VKVQGSDGKF EAAAKNVVAA GTAATTTIVT GYVQLNSPTA YSVSGTGTQA 480
SQVFGNASAA QKSSVASVDI STADGAQNAI AVVDNALAAI DAQRADLGAV QNRFKNTIDN 540
LTNISENATN ARSRIKDTDF AAETAALSKN QVLQQAGTAI LAQANQLPQA VLSLLR
```

| TABLE 2 | |
|---|---|
| Bacterial Strains used in this study | |
| Strain | Description |
| PAK | WT |
| PAO1 | WT |
| WFPA850 | In-frame fliC deletion in PAO1 |
| WFPA852 | In-frame oprF deletion in PAO1 |
| WFPA854 | In-frame oprI deletion in PAO1 |
| WFPA860 | In-frame fliC and oprI deletions in PAO1 |
| WFPA862 | In-frame fliC and oprF deletions in PAO1 |
| WFPA864 | In-frame fliC, oprF, and oprI deletions in PAO1 |
| WFPA866 | In-frame oprF and oprI deletions in PAO1 |
| T69833 | Mucoid CF isolate |
| 1286 | Nonmucoid CF isolate |
| PDO300M | Mucoid PAO1 |
| PDO300NM | Nonmucoid PD0300 deficient in alginate production |

TABLE 3

| Complement-mediated killing of additional P. aeruginosa strains. | |
|---|---|
| Strain | Percent Killed |
| PAK (WT) | 86.5 ± 0.2% |
| 1286 (nonmucoid CF isolate) | 84.3 ± 0.8% |
| PD0300M (mucoid PAO1) | 15.2 ± 1% |
| PD0300NM (alginate deficient PDO300) | 83.4 ± 0.4% |
| T68933 (mucoid CF isolate) | 24.8 ± 0.3% |

That which is claimed is:

1. A nucleic acid encoding a fusion protein comprising: (a) a *Pseudomonas aeruginosa* type A flagellin adjuvant or a *Pseudomonas aeruginosa* type B flagellin adjuvant; and (b) a *Pseudomonas aeruginosa* antigen, the antigen comprising a *Pseudomonas aeruginosa* OprF antigen and a *Pseudomonas aeruginosa* OprI antigen, wherein the *Pseudomonas aeruginosa* antigen is an N-terminal extension of the flagellin adjuvant, wherein the fusion protein is able to activate the TLR5 pathway, and wherein there is no significant difference in the half-maximal stimulation of TNF-α production between *Pseudomonas aeruginosa* type A flagellin, *Pseudomonas aeruginosa* type B flagellin, and the fusion protein.

2. A vector comprising the nucleic acid of claim 1.

3. A host cell comprising the nucleic acid of claim 1.

4. A method of making a fusion protein comprising: (a) a *Pseudomonas aeruginosa* type A flagellin adjuvant or a *Pseudomonas aeruginosa* type B flagellin adjuvant; and (b) a *Pseudomonas aeruginosa* antigen, the antigen comprising a *Pseudomonas aeruginosa* OprF antigen and a *Pseudomonas aeruginosa* OprI antigen, wherein the *Pseudomonas aeruginosa* antigen is an N-terminal extension of the flagellin adjuvant, the method comprising culturing the host cell of claim 3 in a culture medium under conditions sufficient for the fusion protein to be produced, and wherein the nucleic acid is operatively linked to a second nucleic acid sequence which allows for expression of the fusion protein.

5. The nucleic acid of claim 1, wherein the fusion protein comprises:
   (a) a *Pseudomonas aeruginosa* type A flagellin adjuvant; and
   (b) a *Pseudomonas aeruginosa* OprF antigen and a *Pseudomonas aeruginosa* OprI antigen.

6. The nucleic acid of claim 1, wherein the fusion protein comprises:
   (a) a *Pseudomonas aeruginosa* type B flagellin adjuvant; and
   (b) a *Pseudomonas aeruginosa* OprF antigen and a *Pseudomonas aeruginosa* OprI antigen.

7. The nucleic acid of claim 1, wherein the fusion protein is able to activate the TLR5 pathway at nanomolar concentrations of the fusion protein.

8. The nucleic acid of claim 1, wherein the fusion protein is able to activate the TLR5 pathway at picomolar concentrations of the fusion protein.

9. The nucleic acid of claim 1, wherein TNF-α production is stimulated by incubating the fusion protein with RAW 424 (TLR5+) cells.

10. The nucleic acid of claim 1, wherein the *Pseudomonas aeruginosa* antigen comprises SEQ ID NO:3 and SEQ ID NO:9.

11. The nucleic acid of claim 1, wherein the *Pseudomonas aeruginosa* type A flagellin adjuvant comprises full-length *Pseudomonas aeruginosa* type A flagellin and the *Pseudomonas aeruginosa* type B flagellin adjuvant comprises full-length *Pseudomonas aeruginosa* type B flagellin.

12. A nucleic acid encoding a fusion protein comprising:
   (a) a *Pseudomonas aeruginosa* type A flagellin adjuvant or a *Pseudomonas aeruginosa* type B flagellin adjuvant; and
   (b) a *Pseudomonas aeruginosa* antigen, the antigen comprising a *Pseudomonas aeruginosa* OprF antigen and a *Pseudomonas aeruginosa* OprI antigen,
   wherein the fusion protein is able to activate the TLR5 pathway and generate high-affinity antigen-specific IgG for flagellin, OprI, and OprF.

13. The nucleic acid of claim 12, wherein the *Pseudomonas aeruginosa* antigen is an N-terminal extension of the flagellin adjuvant.

14. The nucleic acid of claim 12, wherein the *Pseudomonas aeruginosa* antigen comprises SEQ ID NO:3 and SEQ ID NO:9.

15. The nucleic acid of claim 12, wherein the *Pseudomonas aeruginosa* type A flagellin adjuvant comprises full-length *Pseudomonas aeruginosa* type A flagellin and the *Pseudomonas aeruginosa* type B flagellin adjuvant comprises full-length *Pseudomonas aeruginosa* type B flagellin.

16. A vector comprising the nucleic acid of claim 12.

17. A host cell comprising the nucleic acid of claim 12.

18. A method of making a fusion protein comprising: (a) a *Pseudomonas aeruginosa* type A flagellin adjuvant or a *Pseudomonas aeruginosa* type B flagellin adjuvant; and (b) a *Pseudomonas aeruginosa* antigen, the antigen comprising a *Pseudomonas aeruginosa* OprF antigen and a *Pseudomonas aeruginosa* OprI antigen, wherein the fusion protein is able to activate the TLR5 pathway and generate high-affinity antigen-specific IgG for flagellin, OprI, and OprF, the method comprising culturing the host cell of claim 17 in a culture medium under conditions sufficient for the fusion protein to be produced, and wherein the nucleic acid is operatively linked to a second nucleic acid sequence which allows for expression of the fusion protein.

\* \* \* \* \*